(12) United States Patent
Jahns et al.

(10) Patent No.: US 10,709,529 B2
(45) Date of Patent: Jul. 14, 2020

(54) KIT OF PARTS CONTAINING DENTAL MILL BLANK COLOURING SOLUTION

(71) Applicant: 3M INNOVATIVE PROPERTIES COMPANY, St. Paul, MN (US)

(72) Inventors: Michael Jahns, Gilching (DE); Hans R. Schnagl, Jengen (DE)

(73) Assignee: 3M Innovative Properties Company, St. Paul, MN (US)

( * ) Notice: Subject to any disclaimer, the term of this patent is extended or adjusted under 35 U.S.C. 154(b) by 428 days.

(21) Appl. No.: 15/500,442

(22) PCT Filed: Jul. 30, 2015

(86) PCT No.: PCT/US2015/042839
§ 371 (c)(1),
(2) Date: Jan. 30, 2017

(87) PCT Pub. No.: WO2016/019114
PCT Pub. Date: Feb. 4, 2016

(65) Prior Publication Data
US 2017/0216000 A1    Aug. 3, 2017

(30) Foreign Application Priority Data
Jul. 31, 2014    (EP) ..................................... 14179340

(51) Int. Cl.
| | | |
|---|---|---|
| *A61C 13/00* | (2006.01) | |
| *A61K 6/78* | (2020.01) | |
| *A61K 6/818* | (2020.01) | |
| *A61K 6/824* | (2020.01) | |
| *A61K 6/833* | (2020.01) | |
| *A61K 6/891* | (2020.01) | |
| *A61C 5/20* | (2017.01) | |
| *A61C 5/77* | (2017.01) | |
| *A61C 7/00* | (2006.01) | |

(Continued)

(52) U.S. Cl.
CPC ............ *A61C 13/0022* (2013.01); *A61C 5/20* (2017.02); *A61C 5/77* (2017.02); *A61C 7/00* (2013.01); *A61C 8/0001* (2013.01); *A61C 8/0015* (2013.01); *A61C 8/0048* (2013.01); *A61C 13/082* (2013.01); *A61C 13/26* (2013.01); *A61C 13/277* (2013.01); *A61K 6/78* (2020.01); *A61K 6/818* (2020.01); *A61K 6/824* (2020.01); *A61K 6/833* (2020.01); *A61K 6/891* (2020.01); *C04B 35/4885* (2013.01); *C04B 41/009* (2013.01); *C04B 41/46* (2013.01); *C04B 41/53* (2013.01); *C04B 41/82* (2013.01); *C09D 17/003* (2013.01); *C04B 2235/3217* (2013.01); *C04B 2235/3225* (2013.01); *C04B 2235/3244* (2013.01); *C04B 2235/3298* (2013.01); *C04B 2235/61* (2013.01); *C04B 2235/612* (2013.01); *C04B 2235/725* (2013.01); *C04B 2235/781* (2013.01)

(58) Field of Classification Search
USPC ....................................................... 433/203.1
See application file for complete search history.

(56) References Cited

U.S. PATENT DOCUMENTS

| | | |
|---|---|---|
| 5,453,262 A | 9/1995 | Dawson |
| 5,652,192 A | 7/1997 | Matson |

(Continued)

FOREIGN PATENT DOCUMENTS

| | | |
|---|---|---|
| DE | 20316004 | 3/2004 |
| EP | 2191809 | 6/2010 |

(Continued)

OTHER PUBLICATIONS

Blumenthal, "The Chemical Behavior of Zirconium," 311-338 (1958).

(Continued)

*Primary Examiner* — Matthew M Nelson
(74) *Attorney, Agent, or Firm* — 3M IPC

(57) ABSTRACT

The present invention relates to a kit of parts comprising a dental mill blank comprising a porous zirconia material and a colouring solution for colouring the porous zirconia material. The porous zirconia material comprises Zr oxide calculated as $ZrO_2$: from 80 to 97 wt.-%, Al oxide calculated as $Al_2O_3$: from 0 to 0.15 wt.-%, Y oxide calculated as $Y_2O_3$: from 1 to 10 wt.-%, Bi oxide calculated as $Bi_2O_3$: from 0.01 to 0.2 wt.-%, the porous zirconia material not comprising Fe calculated as $Fe_2O_3$ in an amount of more than 0.01 wt.-%, wt.-% with respect to the weight of the porous zirconia material. The colouring solution comprises solvent(s), colouring agent(s) comprising metal ions selected from Tb, Er, Pr, Mn or combinations thereof, the solution not comprising Fe ions in an amount of more than 0.01 wt.-%, the solution not comprising Bi ions in an amount of more than 0.01 wt.-%, wt.-% with respect to the weight of the colouring solution. The invention also relates to a process of producing a dental restoration, the process comprising the steps: providing a dental mill blank comprising a porous zirconia material as described in any of the preceding claims, machining an article out of the porous zirconia material, the article having the shape of a dental restoration with an outer and inner surface, providing a colouring solution as described in any of the preceding claims, applying the colouring solution to at least portions of the surface of the article having the shape of a dental restoration.

13 Claims, No Drawings

(51) Int. Cl.
  *A61C 8/00* (2006.01)
  *A61C 13/08* (2006.01)
  *A61C 13/271* (2006.01)
  *A61C 13/277* (2006.01)
  *C04B 35/488* (2006.01)
  *C04B 41/00* (2006.01)
  *C04B 41/46* (2006.01)
  *C04B 41/53* (2006.01)
  *C04B 41/82* (2006.01)
  *C04B 41/91* (2006.01)
  *C09D 17/00* (2006.01)

(56) References Cited

U.S. PATENT DOCUMENTS

| | | | |
|---|---|---|---|
| 7,241,437 B2 | 7/2007 | Davidson | |
| 7,985,119 B2 | 7/2011 | Basler | |
| 8,141,217 B2 | 3/2012 | Gubler | |
| 8,541,329 B2 | 9/2013 | Ritzberger | |
| 2002/0156152 A1* | 10/2002 | Zhang | A61K 6/0017 523/115 |
| 2003/0031984 A1* | 2/2003 | Rusin | A61C 13/0004 433/215 |
| 2003/0125189 A1* | 7/2003 | Castro | C04B 33/14 501/127 |
| 2008/0303181 A1 | 12/2008 | Holand | |
| 2012/0012789 A1 | 1/2012 | Yamada | |
| 2012/0214134 A1 | 8/2012 | Khan | |
| 2013/0341812 A1* | 12/2013 | Schechner | A61K 6/0094 264/17 |
| 2014/0367613 A1* | 12/2014 | Mashio | C04B 35/486 252/301.36 |
| 2015/0238291 A1* | 8/2015 | Hauptmann | A61C 13/0022 428/64.1 |

FOREIGN PATENT DOCUMENTS

| | | | | |
|---|---|---|---|---|
| EP | 2387984 | | 11/2011 | |
| EP | 2692311 | | 2/2014 | |
| FR | 2781366 | | 1/2000 | |
| FR | 2781366 A1 * | 1/2000 | | C04B 35/486 |
| WO | WO 2001-13862 | | 3/2001 | |
| WO | WO 2002-45614 | | 6/2002 | |
| WO | WO 2009-085926 | | 7/2009 | |
| WO | WO 2012-125885 | | 9/2012 | |
| WO | WO-2012125885 A1 * | 9/2012 | | A61K 6/0094 |
| WO | WO 2013-022612 | | 2/2013 | |
| WO | WO 2013-094669 | | 6/2013 | |
| WO | WO 2014/046949 | | 3/2014 | |
| WO | WO 2014-164199 | | 10/2014 | |
| WO | WO 2015-084931 | | 6/2015 | |
| WO | WO 2016/019114 | | 2/2016 | |

OTHER PUBLICATIONS

International Search Report for PCT International Application No. PCT/US2015/042839 dated Nov. 2, 2015, 4 pages.

* cited by examiner

KIT OF PARTS CONTAINING DENTAL MILL BLANK COLOURING SOLUTION

FIELD OF THE INVENTION

The invention relates to a kit of parts containing a dental mill blank containing a porous zirconia material having fluorescing properties, and a colouring solution for imparting colour to the zirconia material of the dental mill blank.

BACKGROUND ART

Dental mill blanks based on zirconia ceramic materials are described in various documents and are also commercially available.

Dental mill blanks are typically used for producing dental restorations (e.g. crowns and bridges) by a milling process. The zirconia material, the dental mill blank is made of, is typically in a pre-sintered and porous stage which facilitates its milling. The obtained dental article is then sintered to its final density before it is placed in the mouth of the patient.

Pure zirconia, however, is white and does not match to the natural colour of the tooth in the mouth of a patient.

To address this issue, the milled zirconia material is typically treated with certain colouring solutions before sintering.

Most of the colouring solutions, which are also commercially available, contain iron as colouring ion. Iron ions seem to be a perfect candidate to achieve the desired tooth colour. WO 2012/125885 A1 (3M) relates to a dental ceramic article comprising ZrO2 and Al2O3 and at least one component comprising Mn, Er or mixtures thereof. It is stated that the ceramic article shows enhanced aesthetic appearance compared with ceramic articles of the state of the art.

WO 2013/022612 A1 (3M) relates to a colouring solution for selectively treating the surface of dental ceramics, the solution comprising a solvent, an effect agent and a complexing agent, the effect caused by the effect agent being either colouring, providing fluorescence or a combination thereof. Metal which were found to be useful include Fe, Mn, Er, Pr, Co and Bi.

US 2012/0012789 A1 (Yamada et al.) describes a fluorescent zirconia material comprising at least one kind of Y2SiO5:Ce, Y2SiO5Tb, (Y, Gd, Eu)BO3, Y2O3:EU, YAG:CE, ZnGa2O4:Zn and BaMgAl10O17:EU.

US 2008/0303181 A1 (Holand et al.) describes a dental material shaded to match the colours of natural dentition comprising ZrO2 stabilized with cerium oxide, a colouring agent comprising one or more Fe, Pr, Tb, Er, Nd, Eu, Yb and M, oxides thereof and combinations thereof.

US 2012/0214134 A1 (Khan et al.) relates to a dental article including yttria stabilized tetragonal zirconia polycrystalline ceramic and no more than 0.15 wt.-% of one or more colouring agents of one or more of: Fe, Er, Co, Pr, Tb, Cr, Nd, Ce, V, Eu, Ho, Ni and Cu, oxides thereof and combinations thereof.

FR 2781366 A1 (Norton Desmarquest Fine Ceramics) describes an yttrium-stabilized zirconium dioxide ceramic composition for dental prostheses being coloured with a pigment blend of iron oxide, bismuth oxide and cerium oxide.

U.S. Pat. No. 8,541,329 B2 (Ivoclar) relates to compositions based on ZrO2 and single- and multi-coloured blanks made from oxide ceramics. As a preferred composition based on ZrO2 further contains Pr calculated as Pr2O3 in an amount of 0.0001 to 0.01 wt.-%, Fe calculated as Fe2O3 in an amount of 0.005 to 0.5 wt.-%, Tb calculated as Tb2O3 in an amount of 0.0001 to 0.1 wt.-% and Mn calculated as Mn2O3 in an amount of 0.0001 to 0.1 wt.-%.

EP 2 692 311 A1 (3M) relates to a dental blank comprising a pre-sintered porous zirconia material showing a N2 adsorption and/or desorption of isotherm type IV according to IUPC classification. Various optional oxides including CeO2, Fe2O3 and Bi2O3 may be present in the aerogel used for preparing the porous zirconia material.

However, there is still room for improvement especially with regard to the requirements to be fulfilled with respect to modern dental materials.

Patients and dentists nowadays have an increasing demand for highly aesthetic dental restorations.

DESCRIPTION OF THE INVENTION

One object of the invention described in the present text can be seen in providing a kit of parts containing all necessary items needed for producing highly aesthetic dental restorations.

The dental restoration should not only match the colour of natural teeth but also have a shiny appearance.

This object can be solved by the kit of parts described in the present text and related processes for its production and use.

In one embodiment the present invention features a kit of parts comprising
  a dental mill blank comprising a porous zirconia material,
  a colouring solution for colouring the porous zirconia material,
the porous zirconia material comprising
  Zr oxide calculated as ZrO2: from 80 to 97 wt.-%,
  Al oxide calculated as Al2O3: from 0 to 0.15 wt.-%,
  Y oxide calculated as Y2O3: from 1 to 10 wt.-%,
  Bi oxide calculated as Bi2O3: from 0.01 to 0.2 wt.-%,
the porous zirconia material not comprising Fe calculated as Fe2O3 in an amount of more than 0.01 wt.-%, wt.-% with respect to the weight of the porous zirconia material,
the colouring solution comprising
  solvent(s),
  colouring agent(s) comprising metal ions selected from Tb, Er, Pr, Mn or combinations thereof,
the solution not comprising Fe ions in an amount of more than 0.01 wt.-%,
the solution not comprising Bi ions in an amount of more than 0.01 wt.-%,
wt.-% with respect to the weight of the colouring solution.

The invention also relates to a process of producing a dental restoration, the process comprising the steps of:
  providing a dental mill blank comprising a porous zirconia material as described in the present text,
  machining an article out of the porous zirconia material, the article having the shape of a dental restoration with an outer and inner surface,
  providing a colouring solution as described the present text,
  applying the colouring solution to at least portions of the outer surface of the article having the shape of a dental restoration,
  optionally drying the article,
  optionally sintering the article to obtain a sintered dental restoration.

The invention also relates to a dental article obtainable by the process described in the present text.

The term "dental article" means any article which is to be used in the dental or orthodontic field, especially for producing of or as dental restoration, a tooth model and parts thereof.

Examples of dental articles include crowns (including monolithic crowns), bridges, inlays, onlays, veneers, facings, copings, crown and bridged framework, implants, abutments, orthodontic appliances (e.g. brackets, buccal tubes, cleats and buttons), monolithic dental restorations (i.e. restorations which do not need to be veneered) and parts thereof.

The surface of a tooth is considered not to be a dental article. A dental article should not contain components which are detrimental to the patient's health and thus free of hazardous and toxic components being able to migrate out of the dental article.

By "dental mill blank" is meant a solid block (3-dim article) of material from which a dental article, dental workpiece, dental support structure or dental restoration can and typically is to be machined in any subtractive process, e.g. besides milling also by grinding, drilling etc.

A dental mill blank has a geometrically defined shape and comprises at least one flat surface. A so-called "free form surface" is not regarded as "geometrically defined". In this respect the shape of a dental restoration (e.g. crown or bridge) itself is not regarded as a dental mill blank.

"Zirconia article" shall mean a 3-dimensional article wherein at least one the x, y, z dimension is at least about 5 mm, the article being comprised of at least 80 or at least 90 or at least 95 wt.-% zirconia.

"Ceramic" means an inorganic non-metallic material that is produced by application of heat. Ceramics are usually hard, porous and brittle and, in contrast to glasses or glass ceramics, display an essentially purely crystalline structure.

"Crystalline" means a solid composed of atoms arranged in a pattern periodic in three dimensions (i.e., has long range crystal structure as determined by X-ray diffraction). Crystal structures include tetragonal, monoclinic, cubic zirconia and mixtures thereof.

"Monolithic dental restoration" shall mean a dental ceramic article onto the surface of which no facing or veneer has been attached. That is, the monolithic dental restoration is essentially comprised out of only one material composition. However, if desired a thin glazing layer can be applied.

"Glass" means an inorganic non-metallic amorphous material which is thermodynamically an under-cooled and frozen melt. Glass refers to a hard, brittle, transparent solid. Typical examples include soda-lime glass and borosilicate glass. A glass is an inorganic product of fusion which has been cooled to a rigid condition without crystallizing. Most glasses contain silica as their main component and a certain amount of glass former.

The porous ceramic dental material described in the present text does not contain a glass. "Glass-ceramic" means an inorganic non-metallic material where one or more crystalline phases are surrounded by a glassy phase so that the material comprises a glass material and a ceramic material in a combination or mixture. It is formed as a glass, and then made to crystallize partly by heat treatment. Glass ceramics may refer to a mixture of lithium-, silicon-, and aluminium-oxides.

The porous dental material described in the present text does not contain a glass-ceramic.

A "powder" means a dry, bulk composed of a large number of fine particles that may flow freely when shaken or tilted.

A "particle" means a substance being a solid having a shape which can be geometrically determined. The shape can be regular or irregular. Particles can typically be analysed with respect to e.g. grain size and grain size distribution.

"Density" means the ratio of mass to volume of an object. The unit of density is typically $g/cm^3$. The density of an object can be calculated e.g. by determining its volume (e.g. by calculation or applying the Archimedes principle or method) and measuring its mass.

The volume of a sample can be determined based on the overall outer dimensions of the sample. The density of the sample can be calculated from the measured sample volume and the sample mass. The total volume of the ceramic material can be calculated from the mass of the sample and the density of the used material. The total volume of cells in the sample is assumed to be the remainder of the sample volume (100% minus the total volume of material).

An article is classified as "absorbent" if the article is able to absorb a certain amount of a liquid, comparable to a sponge. The amount of liquid which can be absorbed depends e.g. on the chemical nature of the article, the viscosity of the solvent, the porosity and pore volume of the article. E.g. a pre-sintered ceramic article, that is an article which has not been sintered to full density, is able to absorb a certain amount of liquid. Absorbing of liquids is typically only possible if the article has an open-porous structure.

A "porous material" refers to a material comprising a partial volume that is formed by voids, pores, or cells in the technical field of ceramics. Accordingly an "open-celled" structure of a material sometimes is referred to as "open-porous" structure, and a "closed-celled" material structure sometimes is referred to as a "closed-porous" structure. It may also be found that instead of the term "cell" sometimes "pore" is used in this technical field. The material structure categories "open-celled" and "closed-celled" can be determined for different porosities measured at different material samples (e.g. using a mercury "Poremaster 60-GT" from Quantachrome Inc., USA) according to DIN 66133. A material having an open-celled or open-porous structure can be passed through by e.g. gases.

Typical values for an "open-celled" material are between 15% and 75% or between 18% and 75%, or between 30% and 70%, or between 34% and 67%, or between 40% to 68%, or between 42% and 67%.

The term "closed-celled" relates to a "closed porosity". Closed cells are those cells which are not accessible from the outside and cannot be infiltrated by gases under ambient conditions.

The "average connected pore diameter" means the average size of the open-celled pores of a material. The average connected pore diameter can be calculated as described in the Examples section.

The term "calcining" refers to a process of heating a solid material to drive off at least 90 percent by weight of volatile chemically bond components (e.g., organic components) (vs., for example, drying, in which physically bonded water is driven off by heating). Calcining is done at a temperature below a temperature needed to conduct a pre-sintering step.

The terms "sintering" or "firing" are used interchangeably. A pre-sintered ceramic article shrinks during a sintering step, that is, if an adequate temperature is applied. The sintering temperature to be applied depends on the ceramic material chosen. For $ZrO_2$ based ceramics a typical temperature range is from 1100° C. to 1550° C. Sintering typically includes the densification of a porous material to a less porous material (or a material having less cells) having a higher density, in some cases sintering may also include changes of the material phase composition (for example, a partial conversion of an amorphous phase toward a crystalline phase).

"Isotropic sintering behaviour" means that the sintering of a porous body during the sintering process occurs essentially invariant with respect to the directions x, y and z. "Essentially invariant" means that the difference in sintering behaviour with respect to the directions x, y and z is in a range of not more than +/−5% or +/−2% or +/−1%.

A "solution" shall mean a composition containing solvent with soluble components dissolved therein. The solution is a liquid at ambient conditions.

A "solvent" is any solvent which is able to dissolve the colouring agent. The solvent should be sufficiently chemically stable if combined with the colouring agent. That is, the solvent shall not be decomposed by the other components present in the composition.

"Soluble" means that a component (solid) can be completely dissolved within a solvent. That is, the substance is able to form individual molecules (like glucose) or ions (like sodium cations or chloride anions) when dispersed in water at 23° C. The solution process, however, might take some time, e.g. stirring the composition over a couple of hours (e.g. about 10 or about 20 h) might be required.

"Colouring ions" shall mean ions which have an absorption in the spectrum visible to the human eye (e.g. from 380 to 780 nm), which results in a coloured solution (visible to the human eye), if the colouring ions are dissolved in water (e.g. about 0.6 mol/l) and/or cause a colouring effect in the zirconia article which has been treated with the colouring solution and sintered afterwards.

A solution can be classified as "storage stable", if it remains stable over a considerable long period of time (at least about 4 weeks to more than about 12 months under ambient conditions). A storage stable solution typically does not show any visible (visible to the human eye) precipitation of the colouring agent during storage at ambient conditions (about 23° C., about 1013 mbar) and does not show decomposition of the solution or precipitation of single or multiple components.

A solution can be characterized as "transparent" within the meaning of the invention if a beam of visible light (about 380 to about 780 nm) is not scattered by the solution and cannot be observed by side view (i.e. no Tyndall effect). However, the intensity of the penetrating beam of visible light in direction of the beam may be weakened due to absorption of the light by the colouring ions.

A solution is defined as "coloured", if the a* and b* values (of the L*a*b* CIELAB colour space) are as follows: a* being within a range of above about 5, b* being within a range of above about 20.

A solution is defined as "non-coloured", if the a* and b* values (of the L*a*b* CIELAB colour space) are as follows: a* being within a range of 0±5 or 0±3; b* being within a range of 0±20 or 0±10.

The three coordinates of CIELAB represent the lightness of the colour (L*=0 yields black and L*=100 indicates diffuse white; specular white may be higher), its position between red/magenta and green (a*, negative values indicate green while positive values indicate magenta) and its position between yellow and blue (b*, negative values indicate blue and positive values indicate yellow).

A "fluorescing agent" shall mean an agent showing fluorescence in the region of visible light (380 to 780 nm).

"Sol" refers to a continuous liquid phase containing discrete particles having sizes in a range from 1 nm to 100 nm.

"Diafiltration" is a technique that uses ultrafiltration membranes to completely remove, replace, or lower the concentration of salts or solvents from solutions containing organic molecules. The process selectively utilizes permeable (porous) membrane filters to separate the components of solutions and suspensions based on their molecular size.

The term "aerogel" shall mean a three-dimensional low density (i.e., less than about 20% of theoretical density) solid. An aerogel is a porous material derived from a gel, in which the liquid component of the gel has been replaced with a gas. The solvent removal is often done under supercritical conditions. During this process the network does not substantially shrink and a highly porous, low-density material can be obtained.

The term "tubular reactor" refers to the portion of a continuous hydrothermal reactor system that is heated (i.e., the heated zone). The tubular reactor can be in any suitable shape. The shape of the tubular reactor is often selected based on the desired length of the tubular reactor and the method used to heat the tubular reactor. For example, the tubular reactor can be straight, U-shaped, or coiled. The interior portion of the tubular reactor can be empty or can contain baffles, balls, or other known mixing techniques.

"Casting" means a manufacturing process by which a liquid material (e.g. solution or dispersion) is poured into a mould, which contains a hollow cavity of the desired shape, and then allowed to solidify.

By "machining" is meant milling, grinding, cutting, carving, or shaping a material by a machine. Milling is usually faster and more cost effective than grinding. A "machinable article" is an article having a 3-dimensional shape and having sufficient strength to be machined.

"Ambient conditions" mean the conditions which the inventive solution is usually subjected to during storage and handling. Ambient conditions may, for example, be a pressure of 900 to 1100 mbar, a temperature of 10 to 40° C. and a relative humidity of 10 to 100%. In the laboratory ambient conditions are adjusted to 20 to 25° C. and 1000 to 1025 mbar.

A composition is "essentially or substantially free of" a certain component, if the composition does not contain said component as an essential feature. Thus, said component is not wilfully added to the composition either as such or in combination with other components or ingredient of other components. A composition being essentially free of a certain component usually does not contain that component at all. However, sometimes the presence of a small amount of the said component is not avoidable e.g. due to impurities contained in the raw materials used.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.). Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about".

The term "comprise" shall include also the terms "consist essentially of" and "consists of".

The problem in combining tooth-like colour and tooth-like fluorescence so far was to maintain a high amount of bluish fluorescence while the natural tooth is usually coloured yellow or brown, thus eliminating much of the blue colour.

This problem, however, cannot be evaded completely. But with special combinations of colouring ions, the fluorescence effect can be optimized and a visible fluorescence can be obtained at darker tooth colours than before.

It was found that bismuth is a good additive for adding fluorescence to dental zirconia, because it yields a natural appearing fluorescence spectrum with a maximum emission of blue light, but also emission of green, yellow, orange and red light.

Iron, however, as a colouring agent, with its broad absorption bands, even if present at very low concentrations, eliminates almost all fluorescence provided by bismuth.

Terbium on the other hand possesses narrower absorption bands and a higher yield of fluorescence light can be achieved. Thus, a combination of terbium and bismuth is sometimes preferred.

The combination of certain colouring ions contained in a colouring solution and bismuth ions contained in the zirconia material of a dental mill blank as described in the present text does not only facilitate the manufacturing or machining of tooth coloured dental restorations but also gives the tooth coloured dental restorations a shiny and bright appearance.

By incorporating bismuth ions into the zirconia material of the dental mill blank, the material of the dental mill blank can be provided with fluorescent properties. This, however, is only possible, if there are no or only traces of iron ions present.

Further, it was found that by providing a colouring solution, which is essentially free of iron but comprising at least one out of the three colouring ions erbium, terbium and manganese, it is possible to produce a dental restoration in nearly all desired tooth colours (according to the Vita™ Tooth Shade Guide).

Thus, the kit of parts containing the colouring solution described in the present text is also advantageous from an economic aspect as only a limited number of colouring oxides is needed.

Due to the fact that the porous zirconia material contains Bi ions as fluorescing agent, but is essentially free of colouring ions like Tb, Pr, Er, Mn, Fe and combinations thereof, the fluorescence of the zirconia material is more intense than the fluorescence of a zirconia material containing in addition to Bi ions one of the colouring ions described in the present text.

Thus, the practitioner has more freedom in individually designing the dental restoration by using appropriate colouring solutions.

The solution and the porous zirconia article described in the present text are also useful for producing a dental restoration out of a monolithic block. Producing a dental restoration out of a monolithic pre-sintered zirconia block has to address the need for translucency in the dental appliance, which is usually met by a fluorescing veneering material.

According to the invention, using a fluorescing veneering material is not needed any longer. The material the dental milling block is made of is already fluorescing and the colouring solution is adapted to the material of the dental milling block, i.e. does not block, eliminate or quench the fluorescence. As mentioned above, this is beneficial especially for producing so called "monolithic" restorations which typically consist essentially of zirconia material, without the need of veneering material(s).

It was also found that dental article(s) machined from the porous zirconia material of the dental mill blank(s) can be sintered to final density without negatively affecting physical and mechanical properties like bending strength and/or distortion, despite the fact that further ions are present, which need to fit into the crystalline structure of the sintered dental restoration.

The kit of parts described in the present text comprises a dental mill blank. The dental mill blank comprises a porous zirconia material.

Useful ranges for the x, y and z dimensions of the zirconia material of the dental mill blank include from 5 to 300 or from 8 to 200 mm.

Depending on the mode of production, certain properties of the porous zirconia material of the dental mill blank may vary.

If the porous zirconia material is produced by a pressing technique followed by a heating step (e.g. pre-sintering step), the porous zirconia material fulfils at least one or more, sometimes all of the following parameters:

Not showing a N2 adsorption and/or desorption isotherm with a hysteresis loop;

average grain size: less than about 100 nm or less than about 80 nm or less than about 60 nm;

BET surface: from 2 to 20 $m^2/g$ or from 3 to 14 $m^2/g$ or from 3 to 10 $m^2/g$;

Biaxial flexural strength: from 8 to 80 or from 20 to 50 MPa;

Vickers hardness: from 25 (HV 0.5) to 150 or from 35 to 140 (HV 1).

Further details of the pressing technique and the subsequent pre-sintering or heating step are described further down in the text below.

If the porous zirconia material is produced by a process comprising the step of calcining an aerogel, the porous zirconia material fulfils at least one or more, sometimes all of the following parameters:

(a) showing a N2 adsorption and/or desorption isotherm with a hysteresis loop;

(b) showing a N2 adsorption and desorption of isotherm type IV according to IUPAC classification and a hysteresis loop;

(c) showing a N2 adsorption and desorption isotherm of type IV with a hysteresis loop of type H1 according to IUPAC classification;

(d) showing a N2 adsorption and desorption isotherm of type IV with a hysteresis loop of type H1 according to IUPAC classification in a $p/p_0$ range of 0.70 to 0.95;

(e) average connected pore diameter: from 10 to 100 nm or from 10 to 80 nm or from 10 to 70 nm or from 10 to 50 nm or from 15 to 40;

(f) average grain size: less than about 100 nm or less than about 80 nm or less than about 60 nm or from 10 to 100 or from 15 to 60 nm;

(g) BET surface: from 10 to 200 $m^2/g$ or from 15 to 100 $m^2/g$ or from 16 to 60 $m^2/g$;

(h) Biaxial flexural strength: from 10 to 70 or from 15 to 50 MPa;

(i) Vickers hardness: from 25 (HV 0.5) to 150 or from 35 to 140 (HV 1).

A combination of the following features was found to be particularly beneficial: (a) and (h), or (a) and (b) and (h), or (b) and (c), or (c), (e), (g) and (h).

If desired the above features can be determined as described in the Example section.

Further details of this production method are described in the text further down below.

Surprisingly it was found that material showing a N2 adsorption and/or desorption of isotherm type IV (according to IUPAC classification) and/or adsorption desorption isotherms with a hysteresis loop (especially in a $p/p_0$ range of 0.70 to 0.95) are particularly suitable for producing dental restorations.

The BET surface of porous zirconia materials described in the prior art is typically within a range from 2 to 9 m$^2$/g, whereas the BET surface of the porous zirconia materials described in the present text is preferably above about 10 m$^2$/g.

The average grain size of the zirconia particles in the porous zirconia article described in the present text is small compared to the average grain size of the material of commercially available mill blanks.

A small grain size can be beneficial in that it typically leads to a more homogeneous material (from a chemical perspective), which may also result in more homogeneous physical properties.

Thus, the porous zirconia material described in the present text may have a unique combination of features, which facilitates a reliable production of highly aesthetic dental ceramic articles.

It was found that it can be beneficial for certain properties, if the porous zirconia material has a certain average connected pore diameter. The average connected pore diameter should be in a particular range. It should not be too small and also not be too large.

Due to the nano-scaled particle size and specific average connected pore diameter of the material used for producing the porous zirconia ceramic material of the dental mill blank, this material has a different sintering behaviour compared to the zirconia ceramic material of dental mill blanks which are commercially available (e.g. Lava™ Frame from 3M ESPE) and other zirconia ceramics available on the dental market being typically produced by compacting and pressing zirconia powder (e.g. 3Y-TZP zirconia powder from Tosoh Comp.).

The Vickers hardness of the material is typically also in a particular range.

If the Vickers hardness of the material is too low, the machinability could fall off in quality (edge chipping or breaking of the workpiece) as well as in the ease of manual reworking to individualize the frame of a dental restoration or a monolithic restoration as well.

If the Vickers hardness of the material is too high, the wear of the machining tools may increase in an uneconomic range or the tool could break and destroy the workpiece.

The biaxial flexural strength of the material is typically also in a particular range.

It was found that if the biaxial flexural strength of the material is too low, the material tends to crack during the milling process or during the manual finishing by a dental technician.

On the other hand, if the biaxial flexural strength of the material is too high, the processing of the material by a milling machine is often not possible with reasonable efforts. The milling tool used or the milled material often tend to chip or break. In such a case the shaping of the material had to be done by grinding, e.g. using a Cerec™ grinding machine (Sirona).

It was found that a dental mill blank having the above described features is better machinable than commercially available dental mill blanks, e.g. it produces less dust during the machining process.

The porous zirconia material of the dental mill blank comprises
  Zr oxide calculated as ZrO2: from 80 to 97 wt.-% or from 85 to 95 wt.-%,
  Al oxide calculated as Al2O3: from 0 to 0.15 wt.-% or from 0 to 0.10 wt.-%
  Y oxide calculated as Y2O3: from 1 to 10 wt.-% or from 4 to 8 wt.-%
  Bi oxide calculated as Bi2O3: from 0.01 to 0.20 wt.-% or from 0.03 to 0.15 wt.-%,
the porous zirconia material not comprising Fe calculated as Fe2O3 in an amount of more than 0.01 wt.-% or more than 0.005 wt.-% or more than 0.003 or more than 0.001 wt.-%, wt.-% with respect to the weight of the porous zirconia material.

It can be preferred, if there are no or essentially no iron ions present at all. Thus, the zirconia material is essentially free of iron ions. However, sometimes due to production processes, it is unavoidable that traces of iron ions are still present in the material.

If, however, the content of the iron ions (calculated as oxide) is above the ranges described in the present text, the desired shiny and bright appearance of the dental article cannot be properly achieved.

Without wishing to be bound to a certain theory, it is believed that by using iron as colouring agent, either the UV light needed to initiate the fluorescence or the emitted blue fluorescence light itself or even both are being absorbed by the iron ions and thus lost for the desired visual appearance.

According to a further embodiment, the porous zirconia material is also essentially free of either or all of the following oxides: oxides of V, Mo, Cr, Co, Cu, Pr, Er, Tb, Mn or mixtures thereof.

That is, these oxides are typically not present at all. Traces of utmost 0.01 wt.-% or utmost 0.005 wt.-% or utmost 0.001 wt.-% with respect to the weight of the porous zirconia material may, however, be allowed.

If traces are present, they are present in the following amounts:
  Cr oxide calculated as Cr2O3: less than 0.01 wt.-% or less than 0.001 wt.-%,
  Cu oxide calculated as CuO: less than 0.01 wt.-% or less than 0.001 wt.-%,
  V oxide calculated as V2O5: less than 0.01 wt.-% or less than 0.001 wt.-%,
  Mo oxide calculated as Mo2O3: less than 0.01 wt.-% or less than 0.001 wt.-%,
  Pr oxide calculated as Pr2O3: less than 0.01 wt.-% or less than 0.001 wt.-%,
  Er oxide calculated as Er2O3: less than 0.01 wt.-% or less than 0.001 wt.-%
  Mn oxide calculated as MnO2: less than 0.01 wt.-% or less than 0.001 wt.-% or less than 0.0001 wt.-%,
wt.-% with respect to the weight of the porous zirconia material.

According to a further embodiment, the porous zirconia material is essentially free of any colouring ions or ions which have been added in order to impart a certain colour to the zirconia material.

Besides the porous zirconia material, the dental mill blank may also be characterized by either or all of the following features:
  Shape;
  Dimension.

The dental mill blank has a shape allowing the mill blank to be reversibly attached or fixed to a machining device. Suitable shapes include discs or blocks (e.g. cuboid, cylinder).

E.g. a dental mill blank may have a size of 20 mm to 30 mm in two dimensions, for example may have a diameter in that range, and may be of a certain length in a third dimension. A blank for making a single crown may have a length of 15 mm to 30 mm, and a blank for making bridges may have a length of 40 mm to 80 mm. A typical size of a blank as it is used for making a single crown has a diameter of about 24 mm and a length of about 19 mm. Further, a typical size of a blank as it is used for making bridges has a diameter of about 24 mm and a length of about 58 mm. Besides the above mentioned dimensions, a dental mill blank may also have the shape of a cube, a cylinder or a cuboid. Larger mill blanks may be advantageous if more than one crown or bridge should be manufactured out of one blank. For these cases, the diameter or length of a cylindric or cuboid shaped mill blank may be in a range of 100 to 200 mm, with a thickness being in the range of 10 to 30 mm.

As mentioned above, the porous zirconia material of the dental mill blank can be produced by different methods. According to one embodiment, the porous zirconia material of the dental mill blank can be obtained by a process comprising the steps of
  mixing the powders of the respective oxides contained in the material to obtain a powder mixture and
  pressing the powder mixture.

Alternatively, the porous zirconia material can be obtained by a process comprising the steps of
  mixing a zirconia powder with a solution containing metal ions of Bi,
  drying the mixture to obtain a powder,
  pressing the powder.

Mixing of the oxide powders can be achieved by shaking the powders or putting the powders in a mill (e.g. ball mill) and milling the powders until a homogenous powder mixture is obtained. Further possible mixing equipment can include sieves or granulators.

To facilitate the pressing step(s), pressing aids can be added, if desired.

Suitable pressing aids include binders, lubricating additives and mixtures thereof.

If desired, these aids can be added to the zirconia oxide powder being the main component of the powder mixture.

Suitable metal oxide powders are commercially available from various sources including Tosoh Company (Japan).

The powder mixture is then placed in a mould and pressed into the shape of a dental mill blank.

The pressure to be applied is typically in the range of 150 to 200 MPa. Alternatively, the applied pressure is set so that the pressed ceramic body reaches a certain density, e.g. in the case of zirconia ceramic a density from 2.8 g/cm3 to 3.2 g/cm3.

The article obtained after pressing the powder mixture can be machined or sliced into any desired shape.

According to another embodiment, the porous zirconia material of the dental mill blank can be obtained by a process comprising the step of heat treating or calcining a zirconia aerogel.

Besides zirconia and yttria, the aerogel particles contain as a further component Bi oxide.

The zirconia aerogel can typically be characterized by at least one of the following features:

a. comprising crystalline particles having an average primary particle size in a range from 2 nm to 50 nm or from 2 nm to 30 nm or from 2 to 20 or from 2 to 15 nm;
b. content of crystalline zirconia in the particles: at least 85 mol.-%;
c. having an organic content of at least 3 wt.-% or within a range from 3 to 10 wt.-%;
d. x, y, z dimension: at least 5 or at least 8 or at least 10 or at least 20 mm.

A combination of the features (a) and (b) or (a) and (c) or (a) and (d) or (b) and (c) can be preferred.

The heat treatment for obtaining the porous zirconia material is typically done under the following conditions:
  temperature: from 900 to 1100° C. or from 950 to 1090° C.; from 975 to 1080° C.;
  atmosphere: air or inert gas (e.g. nitrogen, argon);
  duration: until a density of 40 to 60% of the final density of the material has been reached.

The heat treatment or calcining can be conducted in one or more steps.

In a first heat treatment step a binder burn-out could be performed to remove all organic additives from previous process steps to obtain a so called "white body".

In a second heat treatment step the strength and/or the hardness of the white-body could be adjusted to the needs of the follow up processes like machining. In case of a machinable blank the sintering protocol should reflect the interaction of temperature with strength and/or hardness.

If the temperature is too low, the hardness and/or strength of the resulting article might be too low. This can cause problems during a later machining step, e.g. with respect to chipping.

If, on the other hand, the temperature is too high, the hardness and/or strength of the material may become too high. This can cause problems during a later machining step as well, e.g. with respect to the machining tool durability.

The dwell time (that is the time during which the aerogel is kept at that temperature) is helpful as well to tune strength and/or hardness to the specific needs of the chosen machining technology. The dwell time, however, can also be in a range from 0 to 24 h or from 0.1 to 5 h.

If the dwell time is too long, the material of the dental mill blank may become too hard to be machined under reasonable conditions.

According to one embodiment, the porous zirconia material of the dental mill blank or the porous zirconia article can be obtained by a process comprising the steps of
  providing a zirconia sol comprising a solvent and crystalline particles of oxides of Zr, Y, Bi,
  optionally concentrating the zirconia sol to provide a concentrated zirconia sol,
  mixing the sol with a polymerizable organic matrix (e.g. adding a reactive surface modifier to the zirconia sol and optionally an initiator being able to polymerizable surface-modified particles of the zirconia sol);
  optionally casting the zirconia sol into a mould to provide a casted zirconia sol,
  curing the polymerizable organic matrix of the zirconia sol to form a gel (sometimes also referred to as gelation step),
  removing the solvent from the gel (e.g. by first removing water, if present, from the gel via a solvent exchange process to provide an at least partially de-watered gel; followed by a further extraction step where the remaining solvent is extracted e.g. via super critical extraction) to provide the aerogel, optionally cutting the aerogel into smaller pieces,
heat-treating the aerogel to obtain e.g. a machinable material or article.

Producing the porous ceramic zirconia material according to such a process can be beneficial as it often allows for a more homogeneous distribution of the different oxides in the material, if compared to a process using a mixing and milling approach.

Further, the overall chemical composition of the porous ceramic zirconia material can be often better controlled as the raw materials used typically contain less impurities.

In addition, the risk that the material is contaminated by particles resulting from the milling equipment (e.g. mill balls) used, is reduced.

The process of producing the porous ceramic zirconia material typically starts with providing a sol of ZrO2 particles. In the process of making these particles, salts of the fluorescence agent Bi can be added.

To the sol of ZrO2 particles a surface-modifying agent is added, preferably a crosslinkable surface-modifying agent (e.g. a radically reactive surface modifier).

The ZrO2 particles having been surface-modified with a crosslinkable agent can be polymerized, if desired, to provide a composition comprising crosslinked ZrO2 particles.

The crosslinkable surface-modifying agent can be removed later, e.g. during a calcining and/or pre-sintering step.

If desired, the sol is casted into a mould. The mould may have the negative shape of the dental mill block to be provided. Due to size reduction which may be caused by heat treatments of the material, the size of the mould is typically larger than the size of the final dental mill blank.

The shape of the mould is not particularly limited.

The casted zirconia sol is typically treated with heat or radiation in order to start polymerization of the reactive surface modifier. This process usually results in a gel.

If present and desired, water may be removed from the gel, at least partially.

Remaining solvent of the above described sol/gel process is removed, e.g. by supercritical extraction techniques resulting in an aerogel (e.g. in block form).

If desired, the aerogel may be cut into smaller pieces, e.g. having the shape of the dental mill blank.

Zirconia sols are dispersions of zirconia based ceramic particles. The zirconia in the zirconia-based ceramic particles is crystalline, and has been observed to be cubic, tetragonal, monoclinic, or a combination thereof. Because the cubic and tetragonal phases are difficult to differentiate using x-ray diffraction techniques, these two phases are typically combined for quantitative purposes and are referred to as the cubic/tetragonal phase. "Cubic/tetragonal" or "C/T" is used interchangeably to refer to the cubic plus the tetragonal crystalline phases. The percent cubic/tetragonal phase can be determined, for example, by measuring the peak area of the x-ray diffraction peaks for each phase and using Equation (I).

$$\% \ C/T = 100(C/T) \div (C/T + M) \tag{I}$$

In Equation (I), C/T refers to the peak area of the diffraction peak for the cubic/tetragonal phase, M refers to the peak area of the diffraction peak for the monoclinic phase, and % C/T refers to the weight percent cubic/tetragonal crystalline phase. The details of the x-ray diffraction measurements are described more fully in the Example section below.

Typically, at least 50 (in some embodiments, at least 55, 60, 65, 70, 75, 80, 85, 90, or at least 95) weight percent of the zirconia-based particles are present in the cubic or tetragonal crystal structure (i.e., cubic crystal structure, tetragonal crystal structure, or a combination thereof). A greater content of the cubic/tetragonal phase is often desired.

The zirconia particles in the zirconia sols described herein typically have primary particle size in a range of from 2 nm to 50 nm (in some embodiments, 5 nm to 50 nm, 2 nm to 25 nm, 5 nm to 25 nm, 2 nm to 15 nm, or even 5 nm to 15 nm).

Depending on how the zirconia-based particles are prepared, the particles may contain at least some organic material in addition to the inorganic oxides. For example, if the particles are prepared using a hydrothermal approach, there may be some organic material attached to the surface of the zirconia-based particles. Although not wanting to be bound by theory, it is believed that organic material originates from the carboxylate species (anion, acid, or both) included in the feedstock or formed as a byproduct of the hydrolysis and condensation reactions (i.e., organic material is often absorbed on the surface of the zirconia-based particles). For example, in some embodiments, the zirconia-based particles contain up to 15 (in some embodiments, up to 12, 10, 8, or even up to 6) weight percent organic material, based on the weight of the particles.

Although any of a variety of known methods can be used to provide the zirconia-based particles, preferably they are prepared using hydrothermal technology. In one exemplary embodiment, the zirconia-based sols are prepared by hydrothermal treatment of aqueous metal salt (e.g., a zirconium salt, an yttrium salt, a bismuth salt, and an optional lanthanide element salt or aluminum salt) solutions, suspensions or a combination of them.

The aqueous metal salts, which are selected to be soluble in water, are typically dissolved in the aqueous medium. The aqueous medium can be water or a mixture of water with other water soluble or water miscible materials. In addition, the aqueous metal salts and other water soluble or water miscible materials which may be present are typically selected to be removable during subsequent processing steps and to be non-corrosive.

At least a majority of the dissolved salts in the feedstock are usually carboxylate salts rather than halide salts, oxyhalide salts, nitrate salts, or oxynitrate salts. Although not wanting to be bound by theory, it is believed that halide and nitrate anions in the feedstock tend to result in the formation of zirconia-based particles that are predominately of a monoclinic phase rather than the more desirable tetragonal or cubic phases. Further, carboxylates and/or acids thereof tend to be more compatible with an organic matrix material compared to halides and nitrates. Although any carboxylate anion can be used, the carboxylate anion often has no greater than 4 carbon atoms (e.g., formate, acetate, propionate, butyrate, or a combination thereof). The dissolved salts are often acetate salts. The feedstock can further include, for example, the corresponding carboxylic acid of the carboxylate anion. For example, feedstocks prepared from acetate salts often contain acetic acid.

One exemplary zirconium salt is zirconium acetate salt, represented by a formula such as $ZrO((4-n)/2)n+ (CH_3COO-)_n$, where n is in the range from 1 to 2. The zirconium ion may be present in a variety of structures depending, for example, on the pH of the feedstock. Methods of making zirconium acetate are described, for example, in W. B. Blumenthal, "The Chemical Behavior of Zirconium," pp. 311-338, D. Van Nostrand Company, Princeton, N.J. (1958). Suitable aqueous solutions of zirconium acetate are commercially available, for example, from Magnesium Elektron, Inc., Flemington, N.J., that contain, for example, up to 17 weight percent zirconium, up to 18 weight percent zirconium, up to 20 weight percent zirconium, up to 22 weight percent, up to 24 weight percent, up to 26 weight percent, and up to 28 weight percent zirconium, based on the total weight of the solution.

Similarly, exemplary yttrium salts, lanthanide element salts, and aluminum salts often have a carboxylate anion, and are commercially available. Because these salts are typically used at much lower concentration levels than the zirconium salt, however, salts other than carboxylate salts (e.g., acetate salts) may also be useful (e.g., nitrate salts).

The total amount of the various salts dissolved in the feedstock can be readily determined based on the total percent solids selected for the feedstock. The relative amounts of the various salts can be calculated to provide the selected composition for the zirconia-based particles.

Typically, the pH of the feedstock is acidic. For example, the pH is usually less than 6, less than 5, or even less than 4 (in some embodiments, in a range from 3 to 4).

The liquid phase of the feedstock is typically predominantly water (i.e., the liquid phase is an aqueous based medium). Preferably, the water is deionized to minimize the introduction of alkali metal ions, alkaline earth ions, or both into the feedstock. Optionally, water-miscible organic co-solvents are included in the liquid phase in amounts, for example, up 20 weight percent, based on the weight of the liquid phase. Suitable co-solvents include 1-methoxy-2-propanol, ethanol, isopropanol, ethylene glycol, N,N-dimethylacetamide, and N-methyl pyrrolidone.

When subjected to hydrothermal treatment, the various dissolved salts in the feedstock undergo hydrolysis and condensation reactions to form the zirconia-based particles. These reactions are often accompanied with the release of an acidic byproduct. That is, the byproduct is often one or more carboxylic acids corresponding to the zirconium carboxylate salt plus any other carboxylate salt in the feedstock. For example, if the salts are acetate salts, acetic acid is formed as a byproduct of the hydrothermal reaction.

Any suitable hydrothermal reactor can be used for the preparation of the zirconia-based particles. The reactor can be a batch or continuous reactor. The heating times are typically shorter and the temperatures are typically higher in a continuous hydrothermal reactor compared to a batch hydrothermal reactor. The time of the hydrothermal treatments can be varied depending, for example, on the type of reactor, the temperature of the reactor, and the concentration of the feedstock. The pressure in the reactor can be autogeneous (i.e., the vapor pressure of water at the temperature of the reactor), can be hydraulic (i.e., the pressure caused by the pumping of a fluid against a restriction), or can result from the addition of an inert gas such as nitrogen or argon. Suitable batch hydrothermal reactors are available, for example, from Parr Instruments Co., Moline, Ill. Some suitable continuous hydrothermal reactors are described, for example, in U.S. Pat. No. 5,453,262 (Dawson et al.) and U.S. Pat. No. 5,652,192 (Matson et al.).

In some embodiments, the feedstock is passed through a continuous hydrothermal reactor. As used herein, the term "continuous" with reference to the hydrothermal reactor system means that the feedstock is continuously introduced and an effluent is continuously removed from the heated zone. The introduction of feedstock and the removal of the effluent typically occur at different locations of the reactor. The continuous introduction and removal can be constant or pulsed.

The dimensions of tubular reactor can be varied and, in conjunction with the flow rate of the feedstock, can be selected to provide suitable residence times for the reactants within the tubular reactor. Any suitable length tubular reactor can be used provided that the residence time and temperature are sufficient to convert the zirconium in the feedstock to zirconia-based particles. The tubular reactor often has a length of at least 0.5 meter (in some embodiments, at least 1 meter, 2 meters, 5 meters, 10 meters, 15 meters, 20 meters, 30 meters, 40 meters, or even at least 50 meters). The length of the tubular reactor in some embodiments is less than 500 meters (in some embodiments, less than 400 meters, 300 meters, 200 meters, 100 meters, 80 meters, 60 meters, 40 meters, or even less than 20 meters).

Tubular reactors with a relatively small inner diameter are sometimes preferred. For example, tubular reactors having an inner diameter no greater than 3 centimeters are often used because of the fast rate of heating of the feedstock that can be achieved with these reactors. Also, the temperature gradient across the tubular reactor is less for reactors with a smaller inner diameter compared to those with a larger inner diameter. The larger the inner diameter of the tubular reactor, the more this reactor resembles a batch reactor. However, if the inner diameter of the tubular reactor is too small, there is an increased likelihood of the reactor becoming plugged or partially plugged during operation resulting from deposition of material on the walls of the reactor. The inner diameter of the tubular reactor is often at least 0.1 cm (in some embodiments, at least 0.15 cm, 0.2 cm, 0.3 cm, 0.4 cm, 0.5 cm, or even at least 0.6 cm). In some embodiments, the diameter of the tubular reactor is no greater than 3 cm (in some embodiments, no greater than 2.5 cm, 2 cm, 1.5 cm, or even greater than 1 centimeter; in some embodiments, in a range from 0.1 to 2.5 cm, 0.2 cm to 2.5 cm, 0.3 cm to 2 cm, 0.3 cm to 1.5 cm, or even 0.3 cm to 1 cm).

In a continuous hydrothermal reactor, the temperature and the residence time are typically selected in conjunction with the tubular reactor dimensions to convert at least 90 mole percent of the zirconium in the feedstock to zirconia-based particles using a single hydrothermal treatment. That is, at least 90 mole percent of the dissolved zirconium in the feedstock is converted to zirconia-based particles within a single pass through the continuous hydrothermal reactor system.

Alternatively, for example, a multiple step hydrothermal process can be used. For example, the feedstock can be subjected to a first hydrothermal treatment to form a zirconium-containing intermediate and a by-product such as a carboxylic acid. A second feedstock can be formed by removing at least a portion of the by-product of the first hydrothermal treatment from the zirconium-containing intermediate. The second feedstock can then be subjected to a second hydrothermal treatment to form a sol containing the zirconia-based particles. Further details on this process are described, for example, in U.S. Pat. No. 7,241,437 (Davidson et al.).

If a two step hydrothermal process is used, the percent conversion of the zirconium-containing intermediate is typically in a range from 40 to 75 mole percent. The conditions used in the first hydrothermal treatment can be adjusted to provide conversion within this range. Any suitable method can be used to remove at least part of the by-product of the first hydrothermal treatment. For example, carboxylic acids such as acetic acid can be removed by a variety of methods such as vaporization, dialysis, ion exchange, precipitation, and filtration.

When referring to a continuous hydrothermal reactor, the term "residence time" means the average length of time that the feedstock is within the heated portion of the continuous hydrothermal reactor system.

Any suitable flow rate of the feedstock through the tubular reactor can be used as long as the residence time is sufficiently long to convert the dissolved zirconium to zirconia-based particles. That is, the flow rate is often selected based on the residence time needed to convert the zirconium in the feedstock to zirconia-based particles. Higher flow rates are desirable for increasing throughput and for minimizing the deposition of materials on the walls of the tubular reactor. A higher flow rate can often be used when the length of the reactor is increased or when both the length and diameter of the reactor are increased. The flow through the tubular reactor can be either laminar or turbulent.

In some exemplary continuous hydrothermal reactors, the reactor temperature is in the range from 170° C. to 275° C., 170° C. to 250° C., 170° C. to 225° C., 180° C. to 225° C., 190° C. to 225° C., 200° C. to 225° C., or even 200° C. to 220° C. If the temperature is greater than 275° C., the pressure may be unacceptably high for some hydrothermal reactors systems. However, if the temperature is less than 170° C., the conversion of the zirconium in the feedstock to zirconia-based particles may be less than 90 weight percent using typical residence times.

The effluent of the hydrothermal treatment (i.e., the product of the hydrothermal treatment) is a zirconia-based sol. The sol contains at least 3 weight percent zirconia-based particles dispersed, suspended, or a combination thereof in an aqueous medium.

In some embodiments, the zirconia-based particles can contain (a) 0 to 5 mole percent of a lanthanide element oxide, based on total moles of inorganic oxide in the zirconia-based particles, and (b) 1 to 15 mole percent yttrium oxide, based on total moles of inorganic oxide in the zirconia-based particles.

The zirconia-based particles are crystalline and have an average primary particle size no greater than 50 nanometers. In some embodiments, cerium oxide, magnesium oxide, ytterbium oxide, and/or calcium oxide may be used with or in place of the yttria.

In some embodiments, at least a portion of the aqueous-based medium is removed from the zirconia-based sol. Any known means for removing the aqueous-based medium can be used. This aqueous-based medium contains water and often contains dissolved carboxylic acids and/or anions thereof that are present in the feedstock or that are byproducts of the reactions that occur within the hydrothermal reactor. As used herein, the term "carboxylic acids and/or anions thereof" refers to carboxylic acids, carboxylate anions of these carboxylic acids, or mixtures thereof. The removal of at least a portion of these dissolved carboxylic acids and/or anions thereof from the zirconia-based sol may be desirable in some embodiments. The zirconia-based sol can be subjected, for example, to at least one of vaporization, drying, ion exchange, solvent exchange, diafiltration, or dialysis, for example, for concentrating, removal of impurities or to compatibilize with other components present in the sol.

In some embodiments, the zirconia sol (prepared from hydrothermal process or other processes) is concentrated. Along with removing at least a portion of the water present in the effluent, the concentration or drying process often results in the vaporization of at least a portion of the dissolved carboxylic acids.

In other embodiments, for example, the zirconia based sol can be subjected to dialysis or diafiltration. Dialysis and diafiltration both tend to remove at least a portion of the dissolved carboxylic acids and/or anions thereof. For dialysis, a sample of the effluent can be positioned within a membrane bag that is closed and then placed within a water bath. The carboxylic acid and/or carboxylate anions diffuse out of the sample within the membrane bag. That is, these species will diffuse out of the effluent through the membrane bag into the water bath to equalize the concentration within the membrane bag to the concentration in the water bath. The water in the bath is typically replaced several times to lower the concentration of species within the bag. A membrane bag is typically selected that allows diffusion of the carboxylic acids and/or anions thereof but does not allow diffusion of the zirconia-based particles out of the membrane bag.

For diafiltration, a permeable membrane is used to filter the sample. The zirconia particles can be retained by the filter if the pore size of the filter is appropriately chosen. The dissolved carboxylic acids and/or anions thereof pass through the filter. Any liquid that passes through the filter is replaced with fresh water. In a discontinuous diafiltration process, the sample is often diluted to a pre-determined volume and then concentrated back to the original volume by ultrafiltration. The dilution and concentration steps are repeated one or more times until the carboxylic acid and/or anions thereof are removed or lowered to an acceptable concentration level. In a continuous diafiltration process, which is often referred to as a constant volume diafiltration process, fresh water is added at the same rate that liquid is removed through filtration. The dissolved carboxylic acid and/or anions thereof are in the liquid that is removed.

While the majority of the yttrium, bismuth and lanthanum, if present, are incorporated into the crystalline zirconia particles there is a fraction of these metals that can be removed during the diafiltration or dialysis process. The actual composition of a sol after diafiltration may be different than that before dialysis.

A zirconia based sol comprises zirconia-based particles dispersed and/or suspended (i.e., dispersed, suspended, or a combination thereof) in an aqueous/organic matrix. In some embodiments, the zirconia-based particles can be dispersed and/or suspended in the organic matrix without any further surface modification. The organic matrix can be added directly to zirconia based sol. Also, for example, the organic matrix can be added to the zirconia based sol after treatment to remove at least some of the water, after treatment to remove at least some of the carboxylic acids and/or anions thereof, or after both treatments. The organic matrix that is added is often contains a polymerizable composition that is subsequently polymerized and/or crosslinked to form a gel.

In some embodiments, the zirconia based sol can be subjected to a solvent exchange process. An organic solvent having a higher boiling point than water can be added to the effluent. Examples of organic solvents that are suitable for use in a solvent exchange method include 1-methoxy-2-propanol and N-methyl pyrrolidone. The water then can be removed by a method such as distillation, rotary evaporation, or oven drying. Depending on the conditions used for removing the water, at least a portion of the dissolved carboxylic acid and/or anion thereof can also be removed. Other organic matrix material can be added to the treated effluent (i.e., other organic matrix material can be added to the zirconia-based particle suspended in the organic solvent used in the solvent exchange process).

In some embodiments, the zirconia-based sols are treated with a surface modification agent to improve compatibility with the organic matrix material. Surface modification agents may be represented by the formula A-B, where the A group is capable of attaching to the surface of a zirconia-based particle and B is a compatibility group. Group A can be attached to the surface by adsorption, formation of an ionic bond, formation of a covalent bond, or a combination thereof. Group B can be reactive or non-reactive and often tends to impart characteristics to the zirconia-based particles that are compatible (i.e., miscible) with an organic solvent, with another organic matrix material (e.g., monomer, oligomers, or polymeric material), or both. For example, if the solvent is non-polar, group B is typically selected to be non-polar as well. Suitable B groups include linear or branched hydrocarbons that are aromatic, aliphatic, or both aromatic and aliphatic. The surface modifying agents include carboxylic acids and/or anions thereof, sulfonic acids and/or anions thereof, phosphoric acids and/or anions thereof, phosphonic acids and/or anions thereof, silanes, amines, and alcohols. Suitable surface modification agents are further described, for example, in WO 2009/085926 (Kolb et al.), the disclosure of which is incorporated herein by reference.

A surface modification agent can be added to the zirconia-based particles using conventional techniques. The surface modification agent can be added before or after any removal of at least a portion of the carboxylic acids and/or anions thereof from the zirconia-based sol. The surface modification agent can be added before or after removal of the water from the zirconia-based sol. The organic matrix can be added before or after surface modification or simultaneously with surface modification. Various methods of adding the surface modification agent are further described, for example, in WO 2009/085926 (Kolb et al.), the disclosure of which is incorporated herein by reference.

The surface modification reactions can occur at room temperature (e.g., 20° C. to 25° C.) or at an elevated temperature (e.g., up to 95° C.). When the surface modification agents are acids such as carboxylic acids, the zirconia-based particles typically can be surface-modified at room temperature. When the surface modification agents are silanes, the zirconia-based particles are typically surface modified at elevated temperatures.

The organic matrix typically includes a polymeric material or a precursor to a polymeric material such as a monomer or an oligomer having a polymerizable group and a solvent. The zirconia-based particles can be combined with the organic matrix using conventional techniques. For example, if the organic matrix is a precursor to a polymeric material, the zirconia-based particles can be added prior to the polymerization reaction. The composite material containing a precursor of a polymeric material is often shaped before polymerization.

Representative examples of monomers include (meth) acrylate-based monomers, styrene-based monomers, and epoxy-based monomers. Representative examples of reactive oligomers include, polyesters having (meth)acrylate groups, polyurethanes having (meth)acrylate groups, polyethers having (meth)acrylate groups, or acrylics. Representative examples of polymeric material include polyurethanes, poly(meth)acrylates, and polystyrenes.

The zirconia based sols are typically solidified by gelation. Preferably, the gelation process allows large gels to be formed without cracks and gels that can be further processed without inducing cracks. For example, preferably, the gelation process leads to a gel having a structure that will not collapse when the solvent is removed. The gel structure is compatible with and stable in a variety of solvents and conditions that may be necessary for supercritical extraction. Furthermore, the gel structure needs to be compatible with supercritical extraction fluids (e.g., supercritical CO2). In other words, the gels should be stable and strong enough to withstand drying, so as to produce stable gels and give materials that can be heated to burn out the organics, pre-sintered, and densified without inducing cracks. Preferably, the resulting gels have relatively small and uniform pore size to aid in sintering them to high density at low sintering temperatures. However, preferably the pores of the gels are large enough to allow product gases of organic burnout escape without leading to cracking of the gel. Furthermore, the gelation step allows control of the density of the resulting gels aids in the subsequent processing of the gel such as supercritical extraction, organic burnout, and sintering. It is preferable that the gel contain the minimum amount of organic material or polymer modifiers.

The gels described herein contain zirconia-based particles. In some embodiments, the gels contain at least two types of zirconia-based particles varying in crystalline phases, composition, or particle size. We have found, particulate based gels can lead to less shrinkage compared to gels produced form alkoxides which undergo significant and complicated condensation and crystallization reactions during further processing. The crystalline nature allows combinations of different crystal phases on a nanoscale. Applicants have observed that formation of a gel thru polymerization of these reactive particles yield strong, resilient gels. Applicants have also found that the use of mixtures of sols with crystalline particles can allow formation of stronger and more resilient gels for further processing. For example, Applicants observed that a gel comprising a mixture of cubic and tetragonal zirconia particles was less susceptible to cracking during supercritical extraction and organic burnout steps.

The gels comprise organic material and crystalline metal oxide particles, wherein the crystalline metal oxide particles are present in a range from 3 to 20 volume percent, based on the total volume of the gel, wherein at least 70 (in some embodiments, at least 75, 80, 85, 90, 95, 96, 97, 98, or even at least 99; in a range from 70 to 99, 75 to 99, 80 to 99, or even 85 to 99) mole percent of the crystalline metal oxide is $ZrO2$. Optionally, the gels may also include amorphous non-crystalline oxide sources.

In some embodiments, gels described herein, the crystalline metal oxide particles have an average primary particle size in a range from 5 nanometers to 50 nanometers (in some embodiments, in a range from 5 nanometers to 25 nanometers, 5 nanometers to 15 nanometers, or even from 5 nanometers to 10 nanometers). Typically, the average primary particle size is measured by using the X-Ray Diffraction technique. Preferably, the particles are not agglomerated but, it is possible that particles with some degree of aggregation may also be useful.

Exemplary sources of the $ZrO2$, $Y2O3$, $Bi2O3$, and $Al2O3$ include crystalline zirconia based sols prepared by any suitable means. The sols described above are particularly well suited. The $Y2O3$, $Bi2O3$, and $Al2O3$, can be present in the zirconia based particles, and/or present as separate colloidal particles or soluble salts.

In some embodiments, for gels described herein the crystalline metal oxide particles comprise a first plurality of particles, and a second, different plurality of particles (i.e., is distinguishable by average composition, phase(s), microstructure, and/or size).

Typically, gels described herein have an organic content that is at least 3 (in some embodiments, at least 4, 5, 10, 15, or even at least 20) percent by weight, based on the total weight of the gel. In some embodiments, gels described herein have an organic content in a range from 3 to 30, 10 to 30, or even 10 to 20, percent by weight, based on the total weight of the gel.

Optionally, gels described herein comprise at least one of $Y_2O_3$ (e.g., in a range from 1 to 15, 1 to 9, 1 to 5, 6 to 9, 3.5 to 4.5, or even 7 to 8 mole percent of the crystalline metal oxide is $Y_2O_3$), $Bi_2O_3$ (e.g., up to 0.1 mole percent $Bi_2O_3$), $La_2O_3$ (e.g., up to 5 mole percent $La_2O_3$), or $Al_2O_3$ (e.g., up to 0.5 mole percent $Al_2O_3$).

In one exemplary gel the crystalline metal oxide comprises in a range from 1 to 5 mole percent $Y_2O_3$, and in a range from 0.01 to 0.05 mole percent $Bi_2O_3$, and in a range from 0 to 2 mole percent $La_2O_3$, and in a range from 93 to 97 mole percent $ZrO_2$. In another exemplary gel the crystalline metal oxide comprises in a range from 6 to 9 mole percent $Y_2O_3$, and in a range from 0.01 to 0.1 mole percent $Bi_2O_3$, and in a range from 0 to 2 mole percent $La_2O_3$, and in a range from 89 to 94 mole percent $ZrO_2$. In another exemplary gel the crystalline metal oxide comprises in a range from 3.5 to 4.5 mole percent $Y_2O_3$, and in a range from 0.01 to 0.05 mole percent $Bi_2O_3$, and in a range from 0 to 2 mole percent $La_2O_3$, and in a range from 93.5 to 96.5 mole percent $ZrO_2$. In another exemplary gel the crystalline metal oxide comprises in a range from 7 to 8 mole percent $Y_2O_3$, and in a range from 0.01 to 0.1 mole percent $Bi_2O_3$, and in a range from 0 to 2 mole percent $La_2O_3$, and in a range from 90 to 93 mole percent $ZrO_2$. In some embodiments, the amount of optional oxide(s) is in an amount in a range from 10 ppm to 20,000 ppm.

One exemplary method for making gels described herein comprises providing a first zirconia sol comprising crystalline metal oxide particles having an average primary particle size of not greater than 15 nanometers (in some embodiments, in a range from 5 nanometers to 15 nanometers), wherein at least 70 (in some embodiments, at least 75, 80, 85, 90, 95, 96, 97, 98, or even at least 99; in a range from 70 to 99, 75 to 99, 80 to 99, or even 85 to 99) mole percent of the crystalline metal oxide is $ZrO_2$. The sol is optionally concentrated to provide a concentrated zirconia sol.

A co-solvent, surface modifiers and optional monomers are added while stirring to obtain a well dispersed sol. Also, a radical initiator (e.g., ultraviolet (UV) or thermal initiator) is added to the radically polymerizable surface-modified zirconia sol.

The resulting sol is optionally purged with $N_2$ gas to remove oxygen. The resulting sol can be gelled by radiating with actinic or heating at at least one temperature for a time sufficient to polymerize the radically surface-modified zirconia sol comprising the radical initiator to form a gel. Typically the resulting gel is a strong, translucent gel.

In some embodiments the sols for making aerogels described herein comprise zirconia based particles that are surface modified with a radically polymerizable surface treatment agent/modifier.

Exemplary radically polymerizable surface modifiers include acrylic acid, methacrylic acid, beta-carboxyethyl acrylate, and mono-2-(methacryloxyethyl)succinate. An exemplary modification agent for imparting both polar character and reactivity to the zirconia-containing nanoparticles is mono(methacryloxypolyethyleneglycol) succinate. Exemplary polymerizable surface modifiers can be can reaction products of hydroxyl containing polymerizable monomers with cyclic anhydrides such as succinic anhydride, maleic anhydride and pthalic anhydride. Exemplary polymerization hydroxyl containing monomers include hyroxyethyl acrylate, hydroxyethyl methacrylate, hydoxypropyl acrylate, hydoxyproyl methacrylate, hydroxyl butyl acrylate, and hydroxybutyl methacrylate. Acyloxy and methacryloxy functional polyethylene oxide, and polypropylene oxide may also be used as the polymerizable hydroxyl containing monomers. Exemplary polymerizable silanes include alkyltrialkoxysilanes methacryloxyalkyltrialkoxysilanes or acryloxyalkyltrialkoxysilanes (e.g., 3-methacryloxypropyltrimethoxysilane, 3-acryloxypropyltrimethoxysilane, and 3-(methacryloxy)propyltriethoxysilane; as 3-(methacryloxy)propylmethyldimethoxysilane, and 3-(acryloxypropyl)methyldimethoxysilane); methacryloxyalkyldialkylalkoxysilanes or acyrloxyalkyldialkylalkoxysilanes (e.g., 3-(methacryloxy)propyldimethylethoxysilane); mercaptoalkyltrialkoxylsilanes (e.g., 3-mercaptopropyltrimethoxysilane); aryltrialkoxysilanes (e.g., styrylethyltrimethoxysilane); vinylsilanes (e.g., vinylmethyldiacetoxysilane, vinyldimethylethoxysilane, vinylmethyldiethoxysilane, vinyltrimethoxysilane, vinyltriethoxysilane, vinyltriacetoxysilane, vinyltriisopropoxysilane, vinyltrimethoxysilane, and vinyltris(2-methoxyethoxy)silane).

Methods for adding a surface modification agent to the zirconia-containing nanoparticles are known in the art. The surface modification agent can be added, for example, before or after any removal of at least a portion of the carboxylic acids and/or anions thereof from the zirconia-containing sol. The surface modification agent can be added, for example, before or after removal of the water from the zirconia-containing sol. The organic matrix can be added, for example, after surface modification or simultaneously with surface modification.

In one exemplary embodiment, the gel is formed by radical polymerization of the surface modified particles and optional monomers.

The polymerization can be initiated by any suitable means such as thermally or actinic radiation or UV initiators. Exemplary thermal initiators include (2,2'-azobis(2-methylbutyronitrile) (available, for example, under the trade designation "VAZO 67" from E. I. du Pont de Nemours and Company, Wilmington, Del.), azobisisobututyronitrile (available, for example, under the trade designation "Vazo 64" from E. I. du Pont de Nemours and Company), 2,2'-azodi-(2,4-Dimethylvaleronitrile (available, for example, under the trade designation "Vazo 52" from E. I. du Pont de Nemours and Company), and 1,1'-azobis(cyclohexanecabonitrile) (available, for example, under the trade designation "Vazo 88" from E. I. du Pont de Nemours and Company). Peroxides and hydroperoxides (e.g., benzoyl peroxide and lauryl peroxide) may also be useful. The initiator selection may be influenced, for example, by solvent choice, solubility and desired polymerization temperature. A preferred initiator is the 2,2'-azobis(2-methylbutyronitrile) available from E. I. du Pont de Nemours and Company under the trade designation "VAZO 67").

Exemplary UV initiators include 1-hydroxycyclohexyl benzophenone (available, for example, under the trade designation "IRGACURE 184" from Ciba Specialty Chemicals Corp., Tarrytown, N.Y.), 4-(2-hydroxyethoxy)phenyl-(2-hydroxy-2-propyl) ketone (available, for example, under the trade designation "IRGACURE 2529" from Ciba Specialty Chemicals Corp.), 2-hydroxy-2-methylpropiophenone (available, for example, under the trade designation "DAROCURE D111" from Ciba Specialty Chemicals Corp. and bis(2,4,6-trimethylbenzoyl)-phenylposphineoxide (available, for example, under the trade designation "IRGA-CURE 819" from Ciba Specialty Chemicals Corp.).

Liquid or solvent in the gel can be exchanged with a second liquid, for example, by soaking the gel in the second liquid for a time sufficient to allow an exchange to occur. For example, water present in a gel can be removed by soaking the gel in a dry solvent (e.g., dry ethanol).

Aerogels described herein are formed by removing solvent from zirconia gels described herein without excessive shrinkage (e.g., not greater than 10%). The gel structure should be strong enough to withstand at least some shrinkage and cracking during the drying (solvent removal).

The aerogels can be prepared by drying gels via super critical extraction. In some embodiments, the aerogels are prepared by drying gels under supercritical conditions of the solvent used in preparing the gel.

In some embodiments, of aerogels described herein, the crystalline metal oxide particles have an average primary particle size in a range from 2 nm to 50 nm (in some embodiments, 5 nm to 50 nm, 2 nm to 25 nm, 5 nm to 25 nm, 2 nm to 15 nm, or even 5 nm to 15 nm).

Typically, aerogels described herein have an organic content that is at least 3 (in some embodiments, at least 4, 5, 10, 15, or even at least 20) percent by weight, based on the total weight of the aerogel. In some embodiments, aerogels described herein have an organic content in a range from 3 to 30, 10 to 30, or even 10 to 20 percent by weight, based on the total weight of the aerogel.

Optionally, aerogels described herein comprise at least one of $Y_2O_3$ (e.g., in a range from 1 to 15, 1 to 9, 1 to 5, 6 to 9, 3.5 to 4.5, or even 7 to 8) mole percent of the crystalline metal oxide is $Y_2O_3$), $Bi_2O_3$ (e.g., up to 0.1 mole percent $Bi_2O_3$), $Al_2O_3$ (e.g., up to 0.5 mole percent $Al_2O_3$). One exemplary aerogel comprises in a range from 1 to 5 mole percent of the crystalline metal oxide is $Y_2O_3$, and in a range from 0.01 to 0.05 mole percent of the crystalline metal oxide is $Bi_2O_3$, and in a range from 0 to 2 mole percent of the crystalline metal oxide is $La_2O_3$, and in a range from 93 to 99 mole percent of the crystalline metal oxide is $ZrO_2$. Another exemplary aerogel comprises in a range from 6 to 9 mole percent of the crystalline metal oxide is $Y_2O_3$, and in a range from 0.01 to 0.1 mole percent of the crystalline metal oxide is $Bi_2O_3$, and in a range from 0 to 2 mole percent of the crystalline metal oxide is $La_2O_3$, and in a range from 89 to 94 mole percent of the crystalline metal oxide is $ZrO_2$. In another exemplary aerogel the crystalline metal oxide comprises in a range from 3.5 to 4.5 mole percent $Y_2O_3$, and in a range from 0.01 to 0.05 mole percent of the crystalline metal oxide is $Bi_2O_3$, and in a range from 0 to 2 mole percent of the crystalline metal oxide is $La_2O_3$, and in a range from 93.5 to 96.5 mole percent $ZrO_2$. In another exemplary aerogel the crystalline metal oxide comprises in a range from 7 to 8 mole percent $Y_2O_3$, and in a range from 0.01 to 0.1 mole percent of the crystalline metal oxide is $Bi_2O_3$, and in a range from 0 to 2 mole percent of the crystalline metal oxide is $La_2O_3$, and in a range from 90 to 93 mole percent $ZrO_2$. In some embodiments, it is desirable to have sufficient oxides present to so the crack free crystalline metal oxide articles has colouring of a tooth. Aerogels described herein typically have a volume percent of oxide in a range of 3 to 20 (in some embodiments, 3 to 15, 3 to 14, or even 8 to 14) percent. Aerogels with lower volume percents of oxide tend to be very fragile and crack during supercritical drying or subsequent processing. Aerogels with higher oxide contents tend to crack during organic burnout because it is more difficult for volatile by-products to escape from the denser structure.

In some embodiments, aerogels described herein have a surface area in the range of 100 m2/g to 300 m2/g (in some embodiments, 150 m2/g to 250 m2/g), and a continuous pore channel size in a range of 10 nm to 20 nm. In some embodiments, the structure of, aerogels described herein is a composite of oxide particles, 3 nm to 10 nm (in some embodiments, 4 nm to 8 nm) in size and organics composed of acetate groups and polymerized monomers. The amount of organic is typically 10 to 20 weight percent of the aerogel.

Aerogels described herein can be made, for example, by providing a first zirconia sol comprising crystalline metal oxide particles having an average primary particle size of up to 50 nm (in some embodiments, 2 nm to 50 nm, 5 nm to 25 nm, 2 nm to 15 nm, or even 5 nm to 15 nm), wherein at least 70 (in some embodiments, at least 75, 80, 85, 90, 95, 96, 97, 98, or even at least 99; in a range from 70 to 99, 75 to 99, 80 to 99, or even 85 to 99) mole percent of the crystalline metal oxide is $ZrO_2$. The first zirconia sol is then optionally concentrated to provide a concentrated zirconia sol. A co-solvent, surface modifiers and optional monomers are added while stirring to obtain a well dispersed sol, wherein the cosolvent is optional).

A radical initiator (e.g., ultraviolet (UV) or thermal initiator) is added to the radically polymerizable surface-modified zirconia sol. Optionally the resulting sol is purged with N2 gas to remove oxygen. The resulting sol is then gelled by radiating with actinic or heating at at least one temperature for a time sufficient to polymerize the radically surface-modified zirconia sol comprising the radical initiator to form a gel. Typically the resulting gel is a strong, translucent gel. The water, if present, is then removed from the gel via alcohol exchange to provide an at least partially de-watered gel. The gel is then converted to an aerogel by removing the alcohol, if present, from the partially de-watered gel via super critical extraction to provide the aerogel.

In one exemplary embodiment, removing the first liquid solvent from the at least partially de-watered gel comprises replacing the first liquid solvent with a second liquid solvent, then slowly increasing the temperature and pressure of the at least partially de-watered gels until supercritical conditions for the second solvent are obtained, then slowly releasing the pressure to 1 bar to provide the monolithic aerogel.

In some embodiments, the complete exchange of the first liquid solvent with the second solvent is carried out under supercritical conditions. In some embodiments, the first liquid solvent is miscible with the second solvent. This method comprises placing the at least partially de-watered gel into a pressure vessel with a sufficient volume of the first liquid solvent to completely immerse the gel, pumping the second solvent into the autoclave at a temperature above the critical temperature of the second solvent until a pressure greater than the critical pressure of the second solvent is reached, maintaining the supercritical pressure in the pressure vessel for a time sufficient to complete the solvent exchange by pumping an additional quantity of the second solvent into the pressure vessel while simultaneously venting the mixture of the first and second solvents to a separator vessel, then slowly releasing the pressure to 1 bar to provide the monolithic aerogel. Typically, the second solvent is carbon dioxide.

The kit of parts described in the present text contains a colouring solution. The colouring solution is adapted and designed to be used in combination with the zirconia material of the dental mill blank described in the present text.

In certain embodiments the solution described in the present text fulfils at least one or more, sometimes all of the following parameters:
- pH value: from 0 to 9 or from 1 to 8 or from 2 to 7, if the colouring solution contains water;
- viscosity: from 1 to 10,000 mPa*s or from 1 to 6,000 mPa*s or from 1 to 2,000 mPa*s (measured at 23° C.);
- being transparent;
- being coloured.

If desired, these parameters can be determined as outlined in the Example section.

If the solution is a water containing (aqueous) solution, it typically has a pH value in the range of 0 to 9, that is from strong acidic to slightly basic.

If the pH value of the solution is outside this range, it might be difficult to achieve a storage stable solution. In particular, the cations of the non-colouring agent might start to precipitate from the solution.

If the solution does not contain a complexing agent, a pH value in the acidic range is typically preferred. If the solution, however, contains a complexing agent, the pH value may be in a range from slightly acidic to slightly basic (e.g. 4 to 9 or 5 to 8).

The solution has typically an adequate viscosity so that a sufficient amount of solution can not only be applied to the surface of the zirconia article but also is able to migrate into the pores of the zirconia article.

Adjusting the viscosity to a value as indicated above can be beneficial in that the solution can be more accurately applied to particular sections or regions of the porous zirconia article.

If the viscosity of the solution is too high, the solution might not be able to sufficiently enter the pores of the zirconia material. On the other hand, if the viscosity of the solution is too low, the solution might migrate into the pores too rapidly and might diffuse into the whole article.

In a further embodiment the solution is transparent.

In a further embodiment, the solution containing the solvent and the colouring ions show light absorption in the range from 380 to 780 nm. That means, the solution appears coloured to the human eye (in contrast to e.g. water).

The colouring solution comprises a solvent for the colouring ion(s). If desired, mixtures of different solvents can be used.

Suitable solvents include water, alcohols (especially low-boiling alcohols, e.g. with a boiling point below about 100° C.) and ketons.

The solvent should be able to dissolve the colouring ions used.

Specific examples of solvents which can be used for dissolving the cations contained in the solution include water, methanol, ethanol, iso-propanol, n-propanol, butanol, acetone, ethylene glycol, glycerol and mixtures thereof.

Typically, the complexing agent is present in the solution in an amount sufficient to dissolve at least the cations of the colouring agent in the solvent or to prevent precipitation of these cations.

The solvent is typically present in an amount sufficient to dissolve the components contained or added to the solvent.

Colouring Agents

The solution comprises at least one colouring agent not being iron.

The colouring agent is typically added during the process of producing the solution as a salt comprising cations and anions.

The colouring solution may contain only one of the following colouring ions: ions of Er, Pr, Mn or Tb or a combination thereof: Er and Pr; Er and Mn; Er and Tb; Pr and Mn; Pr and Tb; Mn and Tb; Er, Pr and Mn; Er, Pr and Tb; Er, Mn and Tb; Pr, Mn and Tb, Er, Pr, Mn and Tb.

Praseodymium and terbium possess narrower absorption bands than other colouring ions like Fe. Thus, by using either Pr, Tb or a mixture thereof, a higher yield of fluorescence light can be achieved.

Praseodymium as an additive to zirconia produces additional, but sometimes undesired orange fluorescence light, since the desired fluorescence colour is blue or blue/green.

Terbium is sometimes preferred over praseodymium, since terbium does not produce a fluorescence (of an undesired colour) of its own and thus does not influence the intended fluorescence colour caused by the fluorescing agent (like e.g. Bi).

Besides those cations the solution described in the present text may contain in addition colouring agent(s) selected from those listed in the Periodic Table of Elements (in the 18 columns form) and are classified as rare earth elements (including Ce, Nd, Gd, Ho, Tm, Yb and Lu) and/or of the subgroups of the rare earth elements and/or salts of transition metals of the groups 3, 4, 5, 6, 7, 9, 10, 11, as long as they do not influence the fluorescence of the material in a negative way. Elements or ions which annul the desired fluorescence or result in a non-tooth coloured sample should not be contained. Thus, the following elements or ions of those elements which are typically not present include: Sm, Eu, Dy and mixtures thereof.

Anions which can be used include $OAc^-$, $NO_3^-$, $NO_2^-$, $CO_3^{2-}$, $HCO_3^-$, $ONC^-$, $SCN^-$, $SO_4^{2-}$, $SO_3^{2-}$, gluturate, lactate, gluconate, propionate, butyrate, glucuronate, benzoate, phenolate, halogen anions (fluoride, chloride, bromide) and mixtures thereof.

In addition, the colouring solution may comprise at least one or more of the following components:
- complexing agent(s);
- thickening agent(s);
- marker substance(s);
- additive(s);
- and mixtures thereof.

E.g. the colouring solution may contain one or more complexing agent(s).

Adding a complexing agent can be beneficial to improve the storage stability of the solution, accelerate the dissolving process of salts added to the solution and/or increase the amount of salts which can be dissolved in the solution.

The complexing agent is typically able to form a complex with the metal ions being present in the solution. The complex formed should be soluble in the solvent. Typically the complex formed is better soluble in the solvent than in water.

E.g., the complexing agent can be used in an at least stoichiometric ratio with respect to the molar amount of the ions contained in the colouring agent. Good results can be achieved, if the molar ratio of the complexing agent to the cations of the colouring agent is equal to or greater than about 1 or about 2 or about 3.

If the amount of complexing agent used is too low, the colouring agent might not be dissolved entirely. If the amount of complexing agent used is too high, the excess complexing agent itself might remain unsolved.

The complexing agent is usually added as a separate component of the solution. However, it can also be added or be present in form of an anion of the colouring agent.

Examples include acetylacetonate, crown ethers, cryptands, ethylenediaminetriacetate and its salts, ethylene diamine tetraacetate and its salts, nitrilotriacetate and its salts, citric acid and its salts, triethylentetramine, porphin, poly acrylate, poly asparagate, acidic peptides, phthalocyanin, salicylate, glycinate, lactate, propylendiamine, ascorbate, oxalic acid and its salts and mixtures thereof.

Complexing agents having anionic groups as complexing ligands can be preferred. At least parts of the complexing ligands should be anionic. Complexing agents having only uncharged complexing ligands (or even cationic ligands) like pure amines (e.g. ethylendiamin at pH values at 8 to 14) might not yield sufficiently stable solutions.

Typically, the complexing agent is present in the colouring solution in an amount sufficient to dissolve at least the cations of the colouring agent in the solvent or to prevent precipitation of these cations.

The colouring solution may also contain one or more thickening agent(s).
Certain thickening agent(s) can be characterized by at least one of the following features:
viscosity: from about 1 to about 2,000 mPa*s or from about 100 to about 1,500 mPa*s (measured at 23° C. at a shear rate of 50 $s^{-1}$);
free of polymerizable groups like (meth)acrylate groups, epoxy groups, carbon-carbon unsaturated groups;
not containing elements like S, P.

Thickening agent(s) which can be used include polyol(s) (including polyvinyl alcohol), glycol ether(s) (e.g. PEG 200, PEG 400, PEG 600, diethylene glycol methyl ether, diethylene glycol ethyl ether), di- and polyalcohol(s) (including 1,2-propanediol, 1,3-propanediol, glycerol), glycerol ether, polysaccharide(s), xanthan gum, methyl cellulose and mixtures thereof.

Polyethylene glycols which can be used can be represented by the following formula:

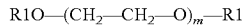

R1O—(CH$_2$—CH$_2$—O)$_m$—R1 with R1=H, Acyl, Alkyl, Aryl, Alkylaryl, Polypropylglycol, Poly-THF, preferably H, Acetyl, Methyl, Ethyl, Propyl, Butyl, Hexyl, Octyl, Nonyl, Decyl, Lauryl, Tridecyl, Myristyl, Palmityl, Stearyl, Oleyl, Allyl, Phenyl, p-Alkylphenyl, Polypropyleneglycol, Poly-THF and
m=about 2 to about 100,000, preferably about 10 to about 20,000, more preferably about 20 to about 2,000.

The average molecular weight (Mw) of the polyethylene glycol should be in the range of about 100 to about 5,000,000, preferably in the range of about 500 to about 1,000,000, more preferably in the range of about 1000 to about 100,000.

The colouring solution may also contain marker substance(s).
Adding a marker substance(s) can be beneficial in order to enhance the visibility of the solution during use, especially, if the solution is transparent and colour-less.

Thus, the practitioner can easily determine to which parts of the surface of the zirconia article the solution has already been applied and which parts have not been treated yet and should remain untreated. On the other hand, if the marker substance is an organic substance, the marker substance(s) will be burnt during a later sintering step and thus not be incorporated into the crystal structure of the zirconia article.

Examples of marker substance(s) which can be used include food colourants like Riboflavin (E101), Ponceau 4R (E124), Green S (E142).

The colouring solution described in the present text may also contain one or more additive(s).

Additives which can be added to the colouring solution include redox-stabilizers (such as methoxy phenol hydrochinone, Topanol A, and mixtures thereof), buffers (such as acetate or amino buffers and mixtures thereof), preservative agents (such as sorbic acid or benzoic acid and mixtures thereof) and mixtures thereof.

There is no need for additive(s) to be present, however, if they are present, they are typically present in an amount which is not detrimental to the purpose to be achieved when applying the solution.

According to one embodiment, the colouring solution does not comprise at least one or all of the following components:
ions of Fe in an amount above 0.01 wt.-% or above 0.005 wt.-% or above 0.003 wt.-% or above 0.001 wt.-%, wt.-% with respect to the weight of the colouring solution;
ions of Bi in an amount above 0.01 wt.-% or above 0.005 wt.-% or above 0.001 wt.-%, wt.-% with respect to the weight of the colouring solution;
ions selected from Dy, Sm, Eu, Cr, Cu, V, Mo or combinations thereof, each in an amount above about 0.01 wt.-% or above about 0.005 wt.-% or above about 0.001 wt.-%, wt.-% with respect to the weight of the colouring solution;
solid particles settling from the solution upon storage for more than about 2 h.

Thus, the solution described in the present text is essentially free of ions of Fe and Bi or only may contain unavoidable traces of Fe and Bi, which may be present in the raw materials used.

Further, the solution does typically also not comprise solid particles which may or will remain on the surface of a zirconia article once the colouring solution is applied to the surface of the zirconia article. Thus, the solution described in the present text is neither a dispersion of solid particles in a solvent nor a slurry.

The colouring solution may contain the respective components in the following amounts:
The solvent(s) may be present in the following amounts:
Lower limit: at least 15 wt.-% or at least 20 wt.-% or at least 30 wt.-%;
Upper limit: utmost 99 wt.-% or utmost 95 wt.-% or utmost 90 wt.-%;
Range: from 15 wt.-% to 99 wt.-% or from 30 wt.-% to 90 wt.-%.

The colouring agent(s) may be present in the following amounts (calculated as ions):
Lower limit: at least 0.05 wt.-% or at least 0.2 wt.-% or at least 0.3 wt.-%;
Upper limit: utmost 10 wt.-% or utmost 8 wt.-% or utmost 5 wt.-%;
Range: from 0.05 wt.-% to 10 wt.-% or from 0.3 wt.-% to 5 wt.-%.

The complexing agent(s) may be present in the following amounts:
Lower limit: at least 0.2 wt.-% or at least 1 wt.-% or at least 2 wt.-%;
Upper limit: utmost 35 wt.-% or utmost 25 wt.-% or utmost 15 wt.-%;
Range: from 0.2 wt.-% to 35 wt.-% or from 2 wt.-% to 15 wt.-%.

The thickening agent(s) may be present in the following amounts:
Lower limit: at least 1 wt.-% or at least 2 wt.-% or at least 3 wt.-%;
Upper limit: utmost 20 wt.-% or utmost 15 wt.-% or utmost 10 wt.-%;
Range: from 1 wt.-% to 20 wt.-% or from 3 wt.-% to 10 wt.-%.

The marking agent(s) may be present in the following amounts:
Lower limit: at least 0.001 wt.-% or at least 0.01 wt.-% or at least 0.1 wt.-%;
Upper limit: utmost 2 wt.-% or utmost 1 wt.-% or utmost 0.5 wt.-%;
Range: from 0.001 wt.-% to 2 wt.-% or from 0.1 wt.-% to 0.5 wt.-%.

The additive(s) may be present in the following amounts:
Lower limit: at least 0.001 wt.-% or at least 0.01 wt.-% or at least 0.1 wt.-%;
Upper limit: utmost 5 wt.-% or utmost 2 wt.-% or utmost 1 wt.-%;
Range: from 0.001 wt.-% to 5 wt.-% or from 0.1 wt.-% to 1 wt.-%.

Unless defined otherwise, wt.-% is based on the amount of the whole colouring solution.

The wt.-% given for the colouring agent is based on the amount of the metal ion(s) contained in the colouring agent.

Thus, the components contained in the solution described in the present text may be present in the following amounts:
Solvent(s): about 15 wt.-% to 99 wt.-% or from 30 wt.-% to 90 wt.-%;
Colouring Agent(s): from 0.05 wt.-% to 10 wt.-% or from 0.5 wt.-% to 5 wt.-% (calculated with respect to the metal ions);
Complexing Agent(s): from 0.2 wt.-% to 35 wt.-% or from 2 wt.-% to 15 wt.-%;
Thickening Agent(s): from 1 wt.-% to 20 wt.-% or from 3 wt.-% to 10 wt.-%;
Marking Agent(s): from 0.001 wt.-% to 2 wt.-% or from 0.1 wt.-% to 0.5 wt.-%;
Additive(s): from 0.001 wt.-% to 5 wt.-% or from 0.1 wt.-% to 1 wt.-%.

The colouring solution described in the present text is typically contained in a receptacle, e.g. a vessel, bottle or flask.

According to a particular embodiment, the receptacle may have the shape of a pen, the pen comprising a housing, a brush tip, a removable cap and a reservoir for storing the solution described in the present text.

The brush tip is typically attached or fixed to the front end of the housing. The reservoir is typically fixed or attached to the rear end of the housing. The removable cap is typically used for protecting the brush tip during storage.

Using a pen may facilitate the application of the colouring solution and will help the practitioner to save time.

Currently, colouring solutions are usually offered in bottles and are applied to porous ceramics with a separate brush or even by dipping the entire ceramic into the colouring solution. This often goes along with a lot of waste of the colouring solution. By using a pen, there will be essentially no waste of the colouring solution.

Further, a pen with a cap will prevent the pen from drying out if not used.

Providing individual pens for individual solutions may further facilitate the application of the composition to the surface of porous dental ceramic(s). Until now, usually only one brush is used and that brush has to be cleaned thoroughly before a further solution is applied.

If, however, one pen for one colour is provided, switching the colours during the application process is quite easy and more save for the dental technician, while mixing of different colours using this kind of equipment is still possible by subsequent application of different colours to the ceramic surface.

The volume of the reservoir may be in a range from about 1 ml to about 10 ml or from about 2 ml to about 5 ml. The reservoir may be removable or fixed to the housing of the pen.

According to one embodiment, the reservoir is exchangeable. The exchangeable reservoir may have the shape of a cartridge or bullet.

The brush tip typically comprises bristles. The material the bristles are made of can be selected from artificial or natural materials. Artificial materials include polyamides (nylon), polyesters and mixtures thereof. Natural materials usually include different kinds of animal hair. The brush tip may be removable or exchangeable, too.

The length of the brush tip extending from the pen is typically within a range from about 5 to about 20 mm or from about 8 to about 15 mm. If the bristles are too short, application of the solution to the inside of a dental restoration may be difficult. If, on the other hand, the bristles are too long, the handling of the brush itself might become impractical for dental applications.

The thickness of the brush tip at its base is typically in the range from about 0.3 to about 5 mm or from about 1 to about 4 mm. If the tip is too broad, application of the solution to the inside of a dental restoration may be difficult. If, on the other hand, the tip is too narrow, the handling of the brush itself might become impractical for dental applications.

Furthermore, if the length and the thickness of the brush tip is either too low or too high, it will be difficult to apply the solution properly, that is either too little to too much of the solution is applied. Both may be detrimental for achieving an accurately coloured dental ceramic.

The shape of the brush tip should be tapered and fan out, if desired, when pressure is applied. Thus, the brush tip should have some flexibility. A brush tip with these properties can be used to draw thin lines and also to paint on larger areas.

A combination of a brush tip comprising bristles having a length from about 8 to about 15 mm with the solution described in the present text having a viscosity above about 200 mPa*s or above about 500 mPa*s (measured at 23° C.) was found to be beneficial. Such a combination facilitates the accurate application of the solution on the surface of the porous dental ceramic(s).

The solution can be produced by mixing its components. This can be done at room temperature or by applying heat and/or while stirring.

Applying heat and/or stirring can be beneficial in order to accelerate the dissolution process of the colouring agent into the solvent. The composition is typically stirred until the cations of the colouring agent(s) are completely dissolved in the solvent. If desired, additives (like those mentioned above) can be added. Undesired precipitations can be removed by filtering.

The kit of parts described in the present text may further comprise either or all of the following components:
instruction for use;
application device(s) useful for applying the colouring solution to the zirconia material of the dental mill blank.
means or holding devices for reversibly fixing or attaching the dental mill blank to a machining device.

The instruction for use typically contains information on machining processes and parameters to be applied and also sintering conditions useful for sintering the machined article to final density as described in the present text.

Examples of application devices or equipment which can be included in the kit of parts described in the present text include brushes, sponges, (hollow) needles, pens, and mixing appliances.

Examples of mixing appliances include mixing wells, trays, plates and slides.

The kit of parts may also contain an instruction of use instructing the practitioner how to apply the solution to the porous zirconia dental article and optionally also how to sinter the coloured zirconia dental article to final density, if desired.

Attaching or fixing the dental mill blank to a machining device, especially to the clamping appliance(s) of such a device, can also be accomplished by providing the blank with suitable means.

Suitable means include frame(s), notch(es), stamp(s) and combinations thereof.

In another embodiment, the dental mill blank is fixed to or contained in a holding device. The holding device containing the dental mill blank may then function as a means for attaching the blank to a machining device.

Fixing of the mill blank to a holding device can be effected by clamping, gluing, screwing and combinations thereof.

Useful holding devices include frames (open and closed) or stumps. Using a holding device may facilitate the production of the dental article with a machining device.
Examples of useful holding devices are described in U.S. Pat. No. 8,141,217 B2 (Gubler et al.), WO 02/45614 A1 (ETH Zurich), DE 203 16 004 U1 (Stuehrenberg), U.S. Pat. No. 7,985,119 B2 (Basler et al.) or WO 01/13862 (3M). The content of these documents with respect to the description of the holding device is herewith incorporated by reference.

The invention is also directed to a process of producing a dental restoration. Such a process typically comprises the following steps:
   providing a dental mill blank comprising a porous zirconia material as described in the present text,
   machining an article out of the porous zirconia material, the article having the shape of a dental restoration with an outer and inner surface as described in the present text,
   providing a colouring solution as described in the present text,
   applying the colouring solution to at least portions of the outer surface of the article having the shape of a dental restoration,
   optionally drying the article,
   optionally sintering the article to obtain a sintered dental restoration as described in the present text.

The machining step is typically being done with or using a milling or grinding device. Those devices are commercially available e.g. from 3M ESPE (Lava™ Form) or Sirona (CEREC™ inLab CAD/CAM).

The machining step can be done with a milling, drilling, cutting, carving, or grinding device.

Useful milling parameters include:
   rotary speed of milling tool: 5,000 to 40,000 revisions/min;
   feed rate: 20 to 5,000 mm/min;
   milling cutter diameter: 0.8 to 4 mm.

The process of producing the zirconia dental article may further comprise the step of sintering the article obtained by machining the porous zirconia dental mill blank.

Sintering will result in a zirconia dental article, sometime also referred to as crystalline metal oxide article.

If conducted, the firing or sintering step should be accomplished under conditions which results in a dental ceramic article having an acceptable tooth like colour (e.g. a colour which fits into the Vita™ shade guide).

Useful sintering conditions can be characterized by one or more of the following parameters:
   temperature: from 900 to 1500° C. or from 1000 to 1400° C. or from 1100° C. to 1350° C. or from 1200° C. to 1400° C. or from 1300° C. to 1400° C. or from 1320° C. to 1400° C. or from 1340° C. to 1350° C.;
   atmosphere: air or inert gas (e.g. nitrogen, argon);
   duration: until a density of about 95 or about 98 or about 99 to about 100% of the final density of the material has been reached;
   dwell time: from 1 to 24 h or from 2 to 12 h;
   pressure: ambient pressure.

A furnace which can be used is the commercially available Lava™ Therm (3M ESPE).

During the firing process the porous dental article is sintered to its final shape, thereby undergoing changes with regard to dimension, density, hardness, bending strength and/or grain size.

The dwell time (that is the time during which the article is kept at that temperature) is not really critical. The dwell time can be zero. The dwell time, however, can also be in a range from 0 to 24 h or from 0.1 to 5 h.

The firing temperature and dwell time (that is, the time period during which a particular temperature is kept) are typically correlated. A higher temperature typically requires only a short dwell time. Thus, the dwell time, may last from 0 (e.g. if the firing temperature is 1550° C.) to 10 h (e.g. if the firing temperature is 1100° C.) or from 0.1 to 8 h.

Generally, the sintering or firing conditions are adjusted such that the sintered dental ceramic article has a density of equal or greater than about 98% compared with the theoretically achievable density.

According to one embodiment, the colouring solution is used for being selectively applied to only parts of the outer surface an article having the shape of a dental restoration. That is, the solution is only applied to parts of the surface of the article but not to the whole surface.

According to another embodiment, the solution is applied to the whole surface of the article having the shape of a dental restoration. This can be achieved, e.g. by dipping the article into the colouring solution.

The porous zirconia article to which the colouring solution is applied is in a pre-sintered stage. Such an article has usually open pores and thus can be described as absorbent.

Selectively applying the solution to the surface of the porous zirconia article is usually achieved by painting e.g. using a brush. However, the solution can also be applied by using a sponge, a fabric, brush-pen or by spraying, equipment which is described in more detail above.

The zirconia article is usually treated with the solution for about 0.5 to about 5 min, preferably from about 1 to about 3 min at room temperature (about 23° C.). Preferably no pressure is used.

A penetration depth of the solution into the article of about 5 mm is considered to be sufficient. If desired, the penetration depth can be determined as follows:

A plastic mesh (mesh size 500 μm) is located in a flat cup, which is filled with a colouring solution containing in addition a certain amount of a colourant (e.g. 100 ppm of Rhodamin B). A test bar of a pre-sintered zirconia material (LAVA™ Frame; 3M ESPE) having a size of Ø=about 24 mm, height=30 mm is placed on the plastic mesh and is soaked with the colouring solution for 2 min; dipping depth:

5 mm. The zirconia material is taken out of the solution and is cut into slices. The cutting edges are finished and the penetration of the solution into the ceramic is analysed with a fluorescence microscope. If the added colourant can be detected over the whole range of the dipping depth and not only in a small border area (about 2 mm), the penetration behaviour of the solution is considered to meet the practitioner's needs.

Drying the treated zirconia material is not absolute necessary, but can be preferred to reduce the time needed for firing and to avoid undesired inhomogenous colour effects. Drying can be effected by simply storing the article on a surface at ambient conditions for a couple of hours (about 1 to about 3 hours).

The invention is also directed to the dental article, in particular a dental restoration, obtainable or obtained by the process described in the present text.

The dental article may have the shape of a crown, bridge, inlay, onlay, veneer, facing, coping, crown and bridged framework, implant, abutment, orthodontic appliances (e.g. brackets, buccal tubes, cleats and buttons) and parts thereof.

The dental mill blank contained in the kit of parts described in the present text can in particular be used for producing monolithic dental restorations.

A after a sintering step the ceramic dental article can usually be characterized by at least one or more of the following features:
  density: fully sintered density of at least about 98.5 (in some embodiments, about 99, 99.5, 99.9, or even at least about 99.99) percent of theoretical density
  Vickers hardness: from 450 MPa to 2200 MPa, or from 500 MPa to 1800 MPa·HV (2);
  Phase content tetragonal phase: from 1 to 100 wt.-% or from 10 to 100 wt.-%; cubic phase: from 30 to 100 wt.-% or from 50 to 90 wt.-%;
  Biaxial flexural strength: from 450 MPa to 2,200 MPa, or from 500 MPa to 2,000 MPa.

One preferred embodiment of the kit of parts described in the present text can be characterized as follows:
the dental mill blank being characterized as follows:
  having the shape of a cubic, cylinder or disc,
  comprising means for attaching the dental mill blank to a machining device,
the porous zirconia material being characterized as follows:
  BET surface: from 2 to 20 m2/g;
  Biaxial flexural strength: from 8 to 80 MPa;
  x, y, z dimension: at least 19 mm;
  Density: 30 to 95% of theoretical density;
  Shrinkage behaviour: isotropic,
the porous zirconia material comprising:
  Zr oxide calculated as ZrO2: from 80 to 97 wt.-%,
  Al oxide calculated as Al2O3: from 0 to 0.15 wt.-%,
  Y oxide calculated as Y2O3: from 1 to 10 wt.-%,
  Bi oxide calculated as Bi2O3: from 0.01 to 0.20 wt.-%,
the porous zirconia material not comprising:
  Fe oxide calculated as Fe2O3 in an amount of more than 0.01 wt.-%,
  Tb oxide calculated as Tb2O3 in an amount of more than 0.01 wt.-%,
  Er oxide calculated as Er2O3 in an amount of more than 0.01 wt.-%,
  Mn oxide calculated as MnO2 in an amount of more than 0.01 wt.-%,
  a glass, glass ceramic or lithium disilicate material,
wt.-% with respect to the weight of the porous zirconia material,
the colouring solution being characterized as follows:
  containing water as solvent in an amount of 20 to 95 wt.-%,
  containing colouring agent(s) comprising ions of Tb, Er, Mn or combinations thereof in an amount of 0.2 to 8 wt.-%, calculated with respect to the weight of the metal ions,
  the solution not comprising Fe ions in an amount above 0.01 wt.-%,
  the solution not comprising Bi ions in an amount above 0.01 wt.-%,
  the solution not comprising ions selected from Dy, Sm, Eu, Cr, Cu, V, Mo or combinations thereof in an amount above about 0.01 wt.-%, wt.-% with respect to the weight of the solution,
  the colouring solution having a pH value in the range of 0 to 9,
  the colouring solution having a viscosity in the range of 1 to 2,000 mPa*s at 23° C.

All components used in the dental composition of the invention should be sufficiently biocompatible, that is, the composition should not produce a toxic, injurious, or immunological response in living tissue.

The dental article described in the present text does typically not contain components or additives which jeopardize the intended purpose to be achieved with the invention. Thus, components or additives added in an amount which finally results in a non-tooth-coloured dental article are usually not contained in the dental article. Typically, an article is characterized as not being tooth coloured if it cannot be allocated a colour from the Vita™ colour code system, known to the person skilled in the art. Additionally, components which will reduce the mechanical strength of the dental restoration to a degree, where mechanical failure will occur, are usually also not included in the dental article.

The zirconia material of the dental mill blank described in the present text does not contain glass, glass ceramic materials, lithium disilicate ceramic materials, or combinations thereof.

Further, the producing of the zirconia material described in the present text does typically also not require the application of a hot isostatic pressing step (HIP).

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate, but not limit, the scope of this invention. Unless otherwise indicated, all parts and percentages are by weight.

EXAMPLES

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).
Measurements
Ion Concentration If desired, the concentration of ions can be determined by X-ray fluorescence sprectrometry (XRF). Some XRF devices offer the possibility to directly measure ion concentrations in liquid solutions, e.g. the ZSX Primus II from Rigaku, Japan.

Fluorescence

The fluorescence properties can be determined using an optical setup comprising the following parts (particularly suited for sharp emission bands): GC America G-Light as light source, irradiating light of around 409 nm wavelength, an Ulbricht sphere, fiber optics from Topsensor Systems as light conductor and an A/D converter. A sample having the shape of a disc (diameter >10 mm, thickness of 1.0 mm) can be used to cover the opening of the Ulbricht sphere. The light emission spectrum of the sample can be measured while trans-illuminating it with exitation radiation (violet light). Excitation radiation of shorter wavelengths is also suited for fluorescence measurements.

Another option is to measure the remission spectrum of the samples e.g. with a spectrophotometer (e.g. Colour i7; X-Rite). Typically two measurements are done: one remission spectrum using irradiation e.g. of the D65 light source including the UV range and one remission spectrum with irradiation e.g. of the D65 light source excluding the UV range. Subsequently both spectra are subtracted from each other, the yielding curve showing the fluorescence effect(s). The area between 410 nm and 540 nm is defined as the area of fluorescence, while the area between 550 nm and 710 nm is defined as the background. The signal intensity of the background area is subtracted from the signal intensity of the fluorescence area to obtain the relative fluorescence intensity.

Choosing this measurement method can be preferred, because it also yields colour information about the sample (i.e. L*a*b* values).

Alternatively, the samples can be placed in an UV-light box used for inspection of e.g. thin layer chromatography plates. If desired, fluorescence can be detected by the human eye as by the lightening up of the sample against the black background.

Average Grain Size

If desired, the average grain size can be determined with the Line Intercept Analysis. FESEM micrographs with 70,000 times magnification are used for grain size measurement. Three or four micrographs taken from different areas of the sintered body are used for each sample. Ten horizontal lines, which are spaced at roughly equal intervals across the height of each micrograph, are drawn. The numbers of grain boundary intercepts observed on each line are counted and used to calculate the average distance between intercepts. The average distance for each line is multiplied by 1.56 to determine the grain size and this value is averaged over all the lines for all micrographs of each sample.

Density

If desired, the density of the sintered material can be measured by an Archimedes technique. The measurements is made on a precision balance (identified as "AE 160" from Mettler Instrument Corp., Hightstown, N.J.) using a density determination kit (identified as "ME 33360" from Mettler Instrument Corp.). In this procedure the sample is first weighed in air (A), then immersed in water (B). The water is distilled and deionized. One drop of a wetting agent (obtained under trade designation "TERGITOL-TMN-6" from Dow Chemical Co., Danbury, Conn.) is added to 250 ml of water. The density is calculated using the formula $\rho=(A/(A-B))\rho 0$, where $\rho 0$ is the density of water. The relative density can be calculated by reference to the theoretical density ($\rho t$) of the material, $\rho_{rel}=(\rho/\rho_t)100$.

Vickers Hardness

If desired, the Vickers hardness can be determined according to ISO 843-4 with the following modifications: The surface of the samples are ground using silicon carbide grinding paper (P400 and P1200). The test forces are adjusted to the hardness level of samples. Used test forces were between 0.2 kg and 2 kg and were applied for 15 s each indentation. A minimum of 10 indentations is measured to determine the average Vickers hardness. The tests can be conducted with a hardness tester Leco M-400-G (Leco Instrumente GmbH).

Biaxial Flexural Strength

If desired, the biaxial flexural strength can be determined according to ISO 6872 (2008) with the following modifications: The sample is sawn into wafers with a thickness of 1 to 2 mm using a dry cut saw. The diameter of the samples should be between 12 and 20 mm. Each wafer is centred on a support of three steel balls with a support diameter of 14 mm. The punch diameter in contact with the wafer is 3.6 mm. The punch is pushed onto the wafer at a rate of 0.1 mm per min. A minimum of 6 samples is measured to determine the average strength. The tests can be conducted in an Instron 5566 universal testing machine (Instron Deutschland GmbH).

Reference Sample 1 (Full Fluorescence):

A composition containing de-ionized water (166.74 g), bismuth acetate (16.63 g) and diammonium EDTA (16.63 g) was prepared.

Bindered $ZrO_2$ (Y-TZP) (60.0 g) was immersed into a mixture of the prepared composition (0.8 g) and water (20.0 g). The mixture was then dried at 60° C. and the resulting powder was sieved.

The powder was pressed into discs. The discs were de-bindered, pre-sintered and then sintered to full density at 1450° C.

Reference Sample 2 (No Fluorescence):

Bindered $ZrO_2$ (TZP) was pressed into discs. The discs were de-bindered, pre-sintered and then sintered to full density at 1450° C.

Inventive Example 1

A composition containing 9.040 g de-ionized water, 0.800 g PEG (Mw 35000), 0.060 g terbium acetate hydrate and 0.100 g triammonium citrate was prepared.

A pre-sintered disc of Reference sample 1 was infiltrated with this composition for 2 min and then left to dry for 3 h. The dried disc was sintered to full density at 1450° C.

Inventive Example 2

A composition containing 9.054 g de-ionized water, 0.800 g PEG (Mw 35000), 0.046 g praseodymium acetate hydrate and 0.100 g triammonium citrate was prepared.

A pre-sintered disc of Reference sample 1 was infiltrated with this composition for 2 min and then left to dry for 3 h. The dried disc was sintered to full density at 1450° C.

Comparative Example

A composition containing 9.156 g de-ionized water, 0.800 g PEG (Mw 35000) and 0.044 g ammonium iron citrate was prepared.

A pre-sintered disc of Reference sample 1 was infiltrated with this composition for 2 min and then left to dry for 3 h.

The dried disc was sintered to full density at 1450° C. and the fluorescence properties of the obtained ceramic were analyzed together with the other samples under UV light.

Findings:

Reference Sample 1: intensive bluish fluorescence.
Reference Sample 2: violet reflection of UV lamp on the white sample.
Inventive Example 1: strong green fluorescence.
Inventive Example 2: strong green/yellow fluorescence.
Comparative Example: very weak fluorescence.

Zirconia material doped with bismuth ions alone shows a strong bluish fluorescence compared to the same material without bismuth doping. This demonstrates that the addition of bismuth ions leads to a fluorescent zirconia material (see Reference Examples 1 and 2).

Zirconia material doped with bismuth ions and coloured with an iron ions based colouring solution was not fluorescent enough for dental applications when the iron concentration was on the level of an A1 tooth colour on the Vita™ Classical Scale or above (e.g. A3, B3) (see Comparative Example).

Compared to this, using a terbium ions based colouring solution combined with a bismuth doped zirconia material can yield darker colours (e.g. B3 tooth colour on the Vita™ Classical Scale) while maintaining a high degree of fluorescence (see Inventive Example 1).

The invention claimed is:

1. A kit of parts for producing a coloured dental article, the kit of parts comprising:
    a dental mill blank comprising a porous zirconia material;
    a colouring solution for colouring the porous zirconia material; and
    a set of instructions;
        the porous zirconia material comprising:
            Zr oxide calculated as $ZrO_2$: from 80 to 97 wt.-%,
            Al oxide calculated as $Al_2O_3$: from 0 to 0.15 wt.-%,
            Y oxide calculated as $Y_2O_3$: from 1 to 10 wt.-%, and
            Bi oxide calculated as $Bi_2O_3$: from 0.01 to 0.2 wt.-%,
        the porous zirconia material not comprising Fe calculated as $Fe_2O_3$ in an amount of more than 0.01 wt.-%, wt.-% with respect to the weight of the porous zirconia material;
        the colouring solution comprising:
            solvent(s), and
            colouring agent(s) comprising metal ions selected from Tb, Er, Pr, Mn, or combinations thereof,
        the colouring solution not comprising Fe ions in an amount of more than 0.01 wt.-%, and
        the colouring solution not comprising Bi ions in an amount of more than 0.01 wt.-%, wt.-% with respect to the weight of the colouring solution;
    wherein the set of instructions direct a user to apply the colouring solution to at least a portion of the dental mill blank to form the coloured dental article, and
    wherein the coloured dental article is fluorescent and producible in more than half of the colours according to the Vita™ Tooth Shade Guide.

2. The kit of parts of claim 1, the at least a portion of the dental mill blank having been machined out of the porous zirconia material.

3. The kit of parts of claim 1, the colouring solution not comprising at least one of the following:
    ions selected from Dy, Sm, Eu, Cr, Cu, V, Mo and combinations thereof, each in an amount above 0.01 wt.-% with respect to the weight of the solution;
    non-soluble particles selected from SiO2, TiO2, ZrO2 and mixtures thereof.

4. The kit of parts of claim 1, the colouring solution comprising in addition at least one of the following components:
    complexing agent(s);
    thickening agent(s);
    marker substance(s);
    additive(s);
    and mixtures thereof.

5. The kit of parts of claim 1, the colouring solution being characterized by at least one of the following features:
    pH value: 0 to 9, if the solution contains water;
    viscosity: 1 to 2,000 mPa*s at 23° C.;
    being transparent;
    being coloured;
    being storage stable.

6. The kit of parts of claim 1, the porous zirconia material not comprising at least one of the following components:
    colouring ion(s) selected from Tb, Er, Pr, Mn, Cu, Cr, V, Mo, Co in an amount of more than 0.01 wt.-% with respect to the weight of the porous zirconia material;
    glass;
    glass ceramic;
    lithium (di)silicate ceramic;
    or combinations thereof.

7. The kit of parts of claim 1, the porous zirconia material fulfils at least one or all of the following parameters:
    (a) not showing a N2 adsorption and/or desorption isotherm with a hysteresis loop;
    (b) average grain size: less than about 100 nm or less than about 80 nm or less than about 60 nm;
    (c) BET surface: from 2 to 20 m2/g;
    (d) biaxial flexural strength: from 8 to 80 MPa;
    (e) Vickers hardness: from 25 (HV 0.5) to 150 (HV 1).

8. The kit of parts of claim 1, the porous zirconia material fulfilling at least one or all of the following parameters:
    (a) showing a N2 adsorption and/or desorption isotherm with a hysteresis loop;
    (b) showing a N2 adsorption and desorption of isotherm type IV according to IUPAC classification and a hysteresis loop;
    (c) showing a N2 adsorption and desorption isotherm of type IV with a hysteresis loop of type H1 according to IUPAC classification;
    (d) showing a N2 adsorption and desorption isotherm of type IV with a hysteresis loop of type H1 according to IUPAC classification in a $p/p_0$ range of 0.70 to 0.95;
    (e) average connected pore diameter: from 10 to 100 nm;
    (f) average grain size: less than about 100 nm;
    (g) BET surface: from 10 to 200 m2/g;
    (h) biaxial flexural strength: from 10 to 70 MPa;
    (i) Vickers hardness: from 25 (HV 0.5) to 150 (HV 1).

9. The kit of parts of claim 1, the dental mill blank being characterized by at least one of the following features:
    shape: cubic or cylindric or disc;
    size: for a cubic shape: more than 19 mm in x, y and z dimension; for a cylindric shape: more than 19 mm in diameter, more than 19 mm in length;
    comprising means for attaching the dental mill blank to a machining device.

10. The kit of parts according to claim 1,
    the dental mill blank being characterized as follows:
        having the shape of a cubic, cylinder or disc;
        comprising means for attaching the dental mill blank to a machining device;

the porous zirconia material being characterized as follows:
  x, y, z dimension: at least 19 mm;
  Density: 30 to 95% of theoretical density;
  Shrinkage behaviour: isotropic;
the porous zirconia material comprising:
  Zr oxide calculated as ZrO2: from 80 to 97 wt.-%;
  Al oxide calculated as Al2O3: from 0 to 0.15 wt.-%;
  Y oxide calculated as Y2O3: from 1 to 10 wt.-%;
  Bi oxide calculated as Bi2O3: from 0.01 to 0.20 wt.-%;
the porous zirconia material not comprising:
  Fe oxide calculated as Fe2O3 in an amount of more than 0.01 wt.-%;
  Tb oxide calculated as Tb2O3 in an amount of more than 0.01 wt.-%;
  Er oxide calculated as Er2O3 in an amount of more than 0.01 wt.-%;
  Mn oxide calculated as MnO2 in an amount of more than 0.01 wt.-%;
  a glass, glass ceramic or lithium disilicate material,
wherein wt.-% with respect to the weight of the porous zirconia material;
the colouring solution being characterized as follows:
  containing water as solvent in an amount of 20 to 95 wt.-%;
  containing colouring agent(s) comprising ions of Tb, Er, Mn or combinations thereof in an amount of 0.2 to 8 wt.-%, calculated with respect to the weight of the metal ions;
  the solution not comprising Fe ions in an amount above 0.01 wt.-%;
  the solution not comprising Bi ions in an amount above 0.01 wt.-%;
  the solution not comprising ions selected from Dy, Sm, Eu, Cr, Cu, V, Mo or combinations thereof in an amount above about 0.01 wt.-%;
  wt.-% with respect to the weight of the solution;
  the colouring solution having a pH value in the range of 0 to 9; and
  the colouring solution having a viscosity in the range of 1 to 2,000 mPa*s at 23° C.

11. The kit of parts of claim 1, wherein the coloured dental article is in the shape of a dental restoration.

12. A process of producing a dental restoration, the process comprising:
  providing a dental mill blank comprising a porous zirconia material of claim 1;
  machining an article out of the porous zirconia material, the article having the shape of a dental restoration with an outer and inner surface;
  providing a colouring solution as described in claim 1;
  applying the colouring solution to at least portions of the outer surface of the article having the shape of a dental restoration;
  optionally drying the article; and
  optionally sintering the article to obtain a sintered dental restoration.

13. The process of claim 12, wherein the dental restoration has the shape of a crown, bridge, inlay, onlay, veneer, facing, coping, crown and bridged framework, implant, abutment, orthodontic appliances or a part thereof.

* * * * *